US012215195B1

(12) United States Patent
Tan et al.

(10) Patent No.: US 12,215,195 B1
(45) Date of Patent: *Feb. 4, 2025

(54) CROSS-LINKABLE THERMOPLASTICS, AND PROCESSES OF MAKING AND USING SAME

(71) Applicant: Government of the United States, as represented by the Secretary of the Air Force, Wright-Patterson AFB, OH (US)

(72) Inventors: Loon-Seng Tan, Centerville, OH (US); David H. Wang, Beavercreek, OH (US); Zhenning Yu, Beavercreek, OH (US); Hilmar Koerner, Beavercreek, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/328,835

(22) Filed: Jun. 5, 2023

Related U.S. Application Data

(62) Division of application No. 16/752,804, filed on Jan. 27, 2020, now Pat. No. 11,840,607.

(Continued)

(51) Int. Cl.
*C08G 73/10* (2006.01)
*B29C 64/118* (2017.01)
(Continued)

(52) U.S. Cl.
CPC .......... *C08G 73/1067* (2013.01); *B33Y 70/00* (2014.12); *C07D 209/50* (2013.01); *C08G 73/1071* (2013.01); *B29C 64/118* (2017.08); *B29C 64/153* (2017.08); *B29K 2079/08* (2013.01); *B29K 2105/0085* (2013.01); *B33Y 10/00* (2014.12); *C08G 2115/00* (2021.01)

(58) Field of Classification Search
None
See application file for complete search history.

(56) References Cited

U.S. PATENT DOCUMENTS

| 4,045,409 A | 8/1977 | Arnold et al. |
| 5,138,028 A | 8/1992 | Paul et al. |

(Continued)

FOREIGN PATENT DOCUMENTS

CN   102848643 A   1/2013

OTHER PUBLICATIONS

Connell, J. W.; Smith, J. G., Jr.; Hergenrother, P. M.: Oligomers and polymers containing phenylethynyl groups. Journal of Macromolecular Science, Reviews in Macromolecular Chemistry and Physics 2000, C40, 207-230.

(Continued)

*Primary Examiner* — Rachel Kahn
(74) *Attorney, Agent, or Firm* — AFMCLO/JAZ; James F. McBride

(57) ABSTRACT

The invention relates to cross-linkable thermoplastics, processes of making such cross-linkable thermoplastics and products comprising such cross-linkable thermoplastics. Such cross-linkable thermoplastics provide articles made by the additive manufacturing (AM) process with increased strength, the desired in use temperature stability and the desired thermo-oxidative stability.

11 Claims, 9 Drawing Sheets

Related U.S. Application Data

(60) Provisional application No. 62/908,168, filed on Sep. 30, 2019.

(51) Int. Cl.
*B29C 64/153* (2017.01)
*B29K 79/00* (2006.01)
*B29K 105/00* (2006.01)
*B33Y 10/00* (2015.01)
*B33Y 70/00* (2020.01)
*C07D 209/50* (2006.01)

(56) References Cited

U.S. PATENT DOCUMENTS

| | | |
|---|---|---|
| 5,606,014 A | 2/1997 | Connell et al. |
| 6,110,411 A | 8/2000 | Clausen et al. |
| 6,124,035 A | 9/2000 | Connell et al. |
| 6,350,817 B1 | 2/2002 | Connell et al. |
| 8,546,614 B1 | 10/2013 | Tan et al. |
| 8,668,981 B2 | 3/2014 | Karst et al. |
| 8,791,227 B1 | 7/2014 | Tan et al. |
| 8,962,890 B1 | 2/2015 | Tan et al. |
| 10,239,254 B1 | 3/2019 | Tan et al. |
| 10,294,255 B1 | 5/2019 | Tan et al. |
| 10,480,098 B2 | 11/2019 | Ishihara et al. |
| 2015/0284498 A1 | 10/2015 | Weiss et al. |
| 2016/0369055 A1 | 12/2016 | Leng et al. |

OTHER PUBLICATIONS

Smith, J. G., Jr.; Connell, J. W.: Chemistry and properties of imide oligomers from phenylethynyl-containing diamines. High Performance Polymers 2000, 12, 213-223.

Sastri, S. B.; Armistead, J. P.; Keller, T. M.; Carbonization of High-Temperature Resins, Carbon, 1993, 31, 4, 617-622.

Jones, K. M.; Keller, T. M.: Synthesis and characterization of multiple phenylethynylbenzenes via cross-coupling with activated palladium catalyst. Polymer 1995, 36, 187-92.

Smith, D. W., Jr.; Babb, D. A.; Snelgrove, R. V.; Townsend, P. H., III; Martin, S. J.: Polynaphthalene Networks from Bisphenols. Journal of the American Chemical Society 1998, 120, 9078-9079.

Fang, X.; Xie, X. Q.; Simone, C. D.; Stevens, M. P.; Scola, D. A.: A Solid-State 13C Nmr Study of the Cure of 13C-Labeled Phenylethynyl End-Capped Polyimides. Macromolecules 2000, 33, 1671-1681.

Beringer, F. M.; Kravetz, L.; Topliss, G. B.: Iodonium Salts Containing Heterocyclic Iodine1-3. The Journal of Organic Chemistry 1965, 30, 1141-1148.

Kraszkiewicz, L.; Sosnowski, M.; Skulski, L.; Easy, inexpensive and effective oxidative iodination of deactivated arenes in sulfuric acid, Tetrahedron 2004, 60, 9113-9119.

Chen, J. C.; Wu, J. A.; Li, S. W.; Chou, S.C.: Highly phenylated polyimides containing 4,4'-diphenylether moiety. Reactive & Functional Polymers 2014, 78, 23-31.

Chen, J. C.; Wu, J. A.; Chang, H. W.; Lee, C. Y.: Organosoluble polyimides derived from asymmetric 2-substituted- and 2,2', 6-trisubstituted-4,4'-oxydianilines. Polymer International 2014, 63, 352-362.

Sastri, S. B.; Keller, T. M.; Jones, K. M.; Armistead, J. P.: Studies on cure chemistry of new acetylenic resins. Macromolecules 1993, 26, 6171-6174.

Chen, J. C.; Rajendran, K.; Chang, Y. H.; Huang, S. W.; Chern, Y. T.: Highly transparent and organosoluble polyimides derived from 2,2'-disubstituted-4,4'-oxydianilines. Journal of Applied Polymer Science 2011, 120, 3159-3170.

Chen, J. C.; Liu, Y. T.; Leu, C. M.; Liao, H. Y.; Lee, W. C.; Lee, T. M.: Synthesis and properties of organosoluble polyimides derived from 2,2'-dibromo- and 2,2',6,6'-tetrabromo-4,4'-oxydianilines. Journal of Applied Polymer Science 2010, 117, 1144-1155.

Grushin, V.V.; Cyclic diaryliodonium ions: old mysteries solved and new applications envisaged Chemical Society Reviews 2000, 29, 315-324.

Hu, B.; William H. Miller, W. H.; Kiel D. Neumann, K.D.; Linstad, E.J.; Dimagno, S.G.; An Alternative to the Sandmeyer Approach to Aryl Iodides Chem. Eur. J. 2015, 21, 6394-6398.

Connell, J. W.; Smith, J. G., Jr.; Hergenrother, P. M.: Properties of imide oligomers containing pendent phenylethynyl groups. High Performance Polymers 1997, 9, 309-321.

Johnston, J. A.; Li, F. M.; Harris, F. W.; Takekoshi, T.; Synthesis and characterization of imide oligomers end- capped with 4-(phenylethynyl)phthalic anhydrides, Polymer, 1994, 2, 4865-4873.

Zhang, Z; Min Li, M; Pan, Y.; Sun, Z.; Thermal Properties of Novel PMR Polyimides Prepared by Copolymerisation, Polymers & Polymer Composites, 2004, 12, 5, 2004.

Smith Jr., J. G.; Connell, J. W.; Hergenrother, P. M.; The Effect of Phenylethynyl Terminated Imide Oligomer Molecular Weight on the Properties of Composites, Journal of Composite Materials, 2000, 34, 7, 614-628.

CROSS-LINKABLE THERMOPLASTICS, AND PROCESSES OF MAKING AND USING SAME

CROSS-REFERENCE TO RELATED APPLICATION

The present application is a divisional of U.S. application Ser. No. 16/752,804 filed Jan. 27, 2020, and claims priority to which in turn claims priority to U.S. Provisional Application Ser. No. 62/908,168 filed Sep. 30, 2019, the contents of both such priority documents being hereby incorporated by reference in their entry.

RIGHTS OF THE GOVERNMENT

The invention described herein may be manufactured and used by or for the Government of the United States for all governmental purposes without the payment of any royalty.

FIELD OF THE INVENTION

The invention relates to cross-linkable thermoplastics, processes of making such cross-linkable thermoplastics and products comprising such cross-linkable thermoplastics.

BACKGROUND OF THE INVENTION

Additive manufacturing processes such as 3-dimensional (3D) printing makes three-dimensional objects by building up material, based upon design data provided from a computer aided design (CAD) system. One technique is to deposit a resolidifiable material in a predetermined pattern, according to design data provided from a CAD system, with the build-up of multiple layers forming the object. The resolidifiable materials can be either in the form of filaments or powdered resins. Fused Filament Fabrication (or FFF) is one type of additive manufacturing (AM) technique. Materials used for FFF are typically thermoplastic (linear) polymers in the form of filaments. The filaments are melted in a "printer" head and extruded onto a deposition surface, and form a solid layer upon cooling. Multiple layers are deposited one atop the other. The complete ensemble of the layers forms the 3-dimensional article. Selective Laser Sintering (SLS) is another type of AM technique that uses a laser as the power source to sinter powdered material, aiming the laser focus automatically at points in space defined by a 3D model, binding the material together to create a solid structure. For hot environment applications such as those that can be found in aerospace applications, state of the art 3D printed thermoplastic articles lack key properties that enable use as engine externals or brackets and fixtures in cooler sections of an engine, ducting for cabin air, etc. Currently, the thermoplastic materials commonly used in FFF or SLS technology are limited in their use temperatures, have insufficient strength, and have poor thermo-oxidative stability. For example, state of the-art 3D filament printable aerospace grade thermoplastics such as ULTEM™ 1010, and ULTEM™ 9085 have use temperatures of 190° C. and 160° C., respectively, and are susceptible to creep during the 3D printing process. Accordingly, there is a need for new materials and methods for use in FFF, SLS, and other.

Applicants recognized that the source of the aforementioned problems was due to the lack of covalent bonding in and between the layers of 3D thermoplastic material that are laid down or deposited during the AM process. As a result of such recognition, Applicants produced a cross-linkable thermoplastic that not only provides increased strength, but also provides the desired improvement in use temperature capability and thermo-oxidative stability. While not being bound by theory, Applicants believe that the aforementioned improvements arise from the crosslinking groups Applicants have engineered into their cross-linkable thermoplastic.

SUMMARY OF THE INVENTION

The invention relates to cross-linkable thermoplastics, processes of making such cross-linkable thermoplastics and products comprising such cross-linkable thermoplastics. Such cross-linkable thermoplastics provide articles made by the AM process with increased strength, the desired improvement in use temperature capability and the desired thermo-oxidative stability.

BRIEF DESCRIPTION OF THE DRAWINGS

The accompanying drawings, which are incorporated in and constitute a part of this specification, illustrate embodiments of the invention and, together with the summary given above, and the detailed description given below, serve to explain the invention.

Figure 1A:
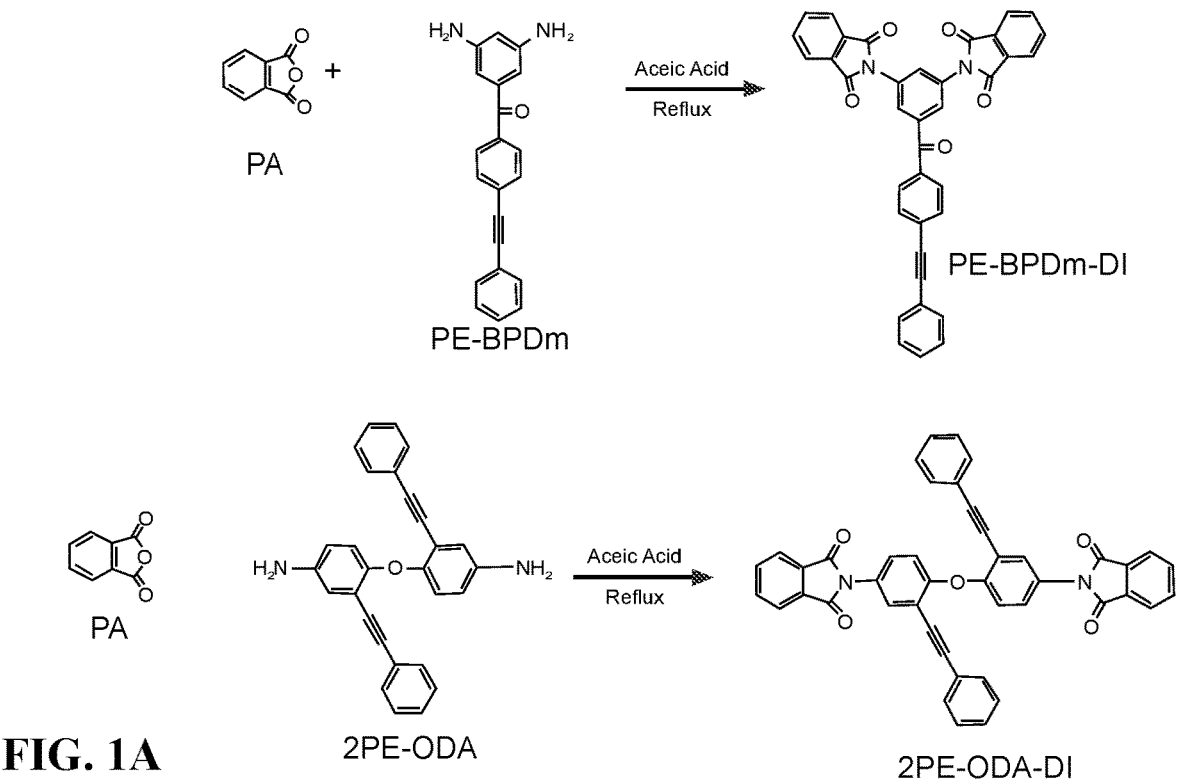
FIG. 1A depicts a scheme for the synthesis of 1,3-N,N-diphathalimido-4'phenylethynyl-benzophenone (PE-BPDm-DI) and 3,3'-bis(phenylethynyl)-4,4'-bis-N,N'-(phthalimide) ether (2PE-ODA-DI).

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Definitions

Unless specifically stated otherwise, as used herein, the terms "a", "an" and "the" mean "at least one"

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cross-Linkable Thermoplastics and Articles Comprising Said Cross-Linkable Thermoplastics and Additive Manufacturing Methods of Making Said Articles For purposes of this specification, headings are not considered paragraphs and thus this paragraph is Paragraph 0024 of the present specification. The individual number of each paragraph above and below this paragraph can be determined by reference to this paragraph's number. In this paragraph 0024. Applicants disclose a cross-linkable thermoplastic having the following structure:

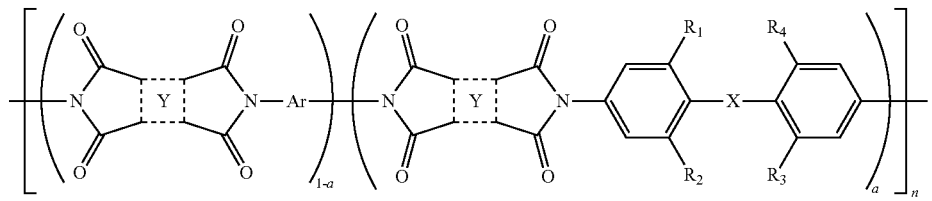

wherein a) each X is independently O, $CH_2$, or $C=O$;

b) $R_1$, $R_2$, $R_3$, and $R_4$ are each independently H or phenylethynyl;

c) each Y is independently selected from one of the following moieties:

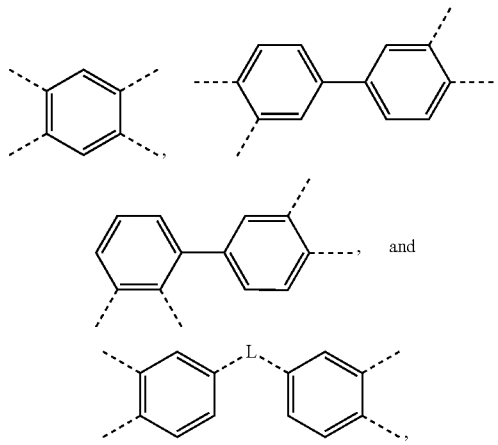

where each L is independently a bivalent linker selected from the one of following moieties: O, $C=O$, $SO_2$, $C(CF_3)_2$, $C(CF_3)Ph$, and $-O\text{-}(pC_6H_4)-C(CF_3)_2\text{-}(pC_6H_4)-O-$;

d) each Ar is independently:

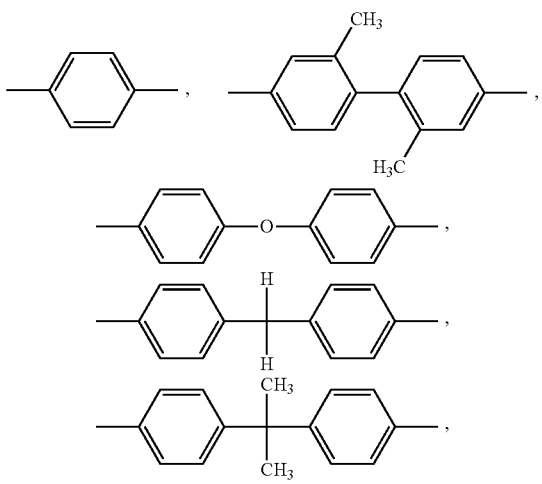

-continued

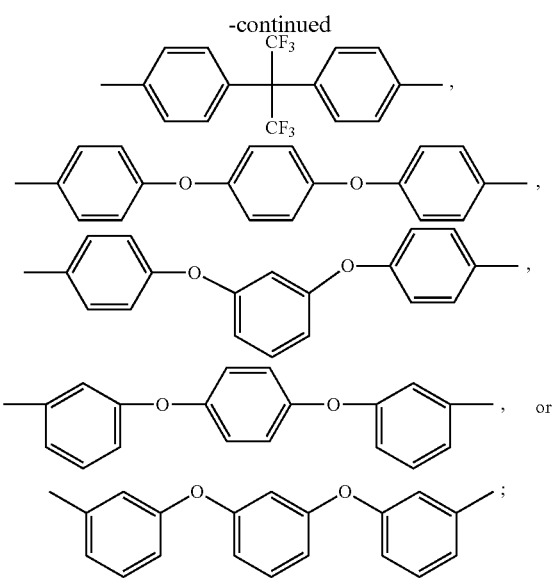

and
e) each a is from about 0.01 to about 1, preferably a is from about 0.05 to about 1, more preferably a is from about 0.1 to about 1; and
f) n is an integer from about 3 to about 200, preferably n is an integer from about 5 to about 100, more preferably n is an integer from about 5 to about 50.

Applicants disclose the cross-linkable thermoplastic of Paragraph 0024, said cross-linkable thermoplastic having a thermal cross-link on set temperature of about 250° C. to about 350° C., preferably said cross-linkable thermoplastic has a thermal cross-link on set temperature of about 275° C. to about 350° C., more preferably said cross-linkable thermoplastic has a thermal cross-link on set temperature of about 300° C. to about 350° C.

Applicants disclose the cross-linkable thermoplastic of Paragraphs 0024 through 0024, said cross-linkable thermoplastic having a thermal cure temperature of 300° C. to about 450° C., preferably said cross-linkable thermoplastic has a thermal cure temperature of 350° C. to about 450° C., more preferably said cross-linkable thermoplastic has a thermal cure temperature of 350° C. to about 425° C.

Applicants disclose an article comprising a cross-linkable thermoplastic according to Paragraphs 0024 through 0026, said thermoplastic being crosslinked, preferably said article is selected from the group consisting of aerospace articles, power generators, electronic device, more preferably said article is selected from the group consisting of a jet engine part, preferably a stator, a jet trailing edge, a jet leading edge, a rocket engine casing, sound proofing, heat insulator, a turbine generator casing, circuit board.

Applicants disclose a jet, rocket, power plant, space station or satellite comprising an article according to Paragraph 0027.

Applicants disclose a process of making an article comprising:
a) laser sintering said laser sintering comprising:
(i) laser sintering a cross-linkable thermoplastic according to Paragraphs 0024 through 0026 a plurality of times to form an article, preferably said cross-linkable thermoplastic being a powder having an average particle size of 50 microns and particle size distribution of +10 microns; and
(ii) curing said article by subjecting said article to a cure cycle that comprises heating said article, preferably said heating comprises a plurality of heating ramps and ramp hold times; or
b) fused deposition modeling, said fused deposition modeling comprising:
(i) fused deposition modeling a cross-linkable thermoplastic according to Paragraphs 0024 through 0026 a plurality of times to form an article, preferably said cross-linkable thermoplastic is a filament having a diameter of about 50 microns to about 10 mm, more preferably said cross-linkable thermoplastic is a filament having a diameter of about 1 mm to about 3 mm, most preferably said cross-linkable thermoplastic is a filament having a diameter of about 1.50 microns to about 2 mm, most preferably said cross-linkable thermoplastic is a filament having a diameter of 1.75 mm; and
(ii) curing said article by subjecting said article to a cure cycle that comprises heating said article, preferably said heating comprises a plurality of heating ramps and ramp hold times.

The teachings found in U.S. Pat. Nos. 6,110,411 A and 10,480098 B2 can be used to transform the cross-linkable thermoplastic according to Paragraphs 0024 through 0026 into cross-linkable thermoplastic powders and filaments that are suitable for use in the process of this Paragraph 0029.

Processes of Making Cross-Linkable Thermoplastics

Applicants disclose a process of making a cross-linkable thermoplastic comprising
a) thermally imidizing, and/or chemically imidizing a solution comprising:
(i) a first monomer having the following structure

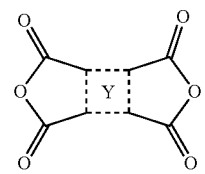

Y is selected from one of the following moieties:

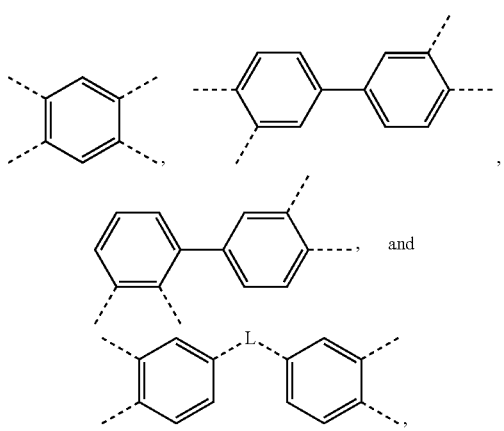

where L is a bivalent linker selected from the one of following moieties: O, C=O, $SO_2$, $C(CF_3)_2$, $C(CF_3)$Ph, and —O-($pC_6H_4$)—$C(CF_3)_2$-($pC_6H_4$)—O—;

(ii) a second monomer having the following structure

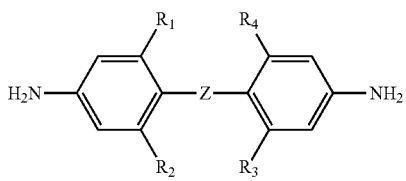

each Z is independently O, $CH_2$, or $C{=}O$;
$R_1$, $R_2$, $R_3$, and $R_4$ are each independently H or phenylethynyl;
(iii) optionally, a third monomer having the following structure, $H_2N-Ar-NH_2$
wherein Ar is:

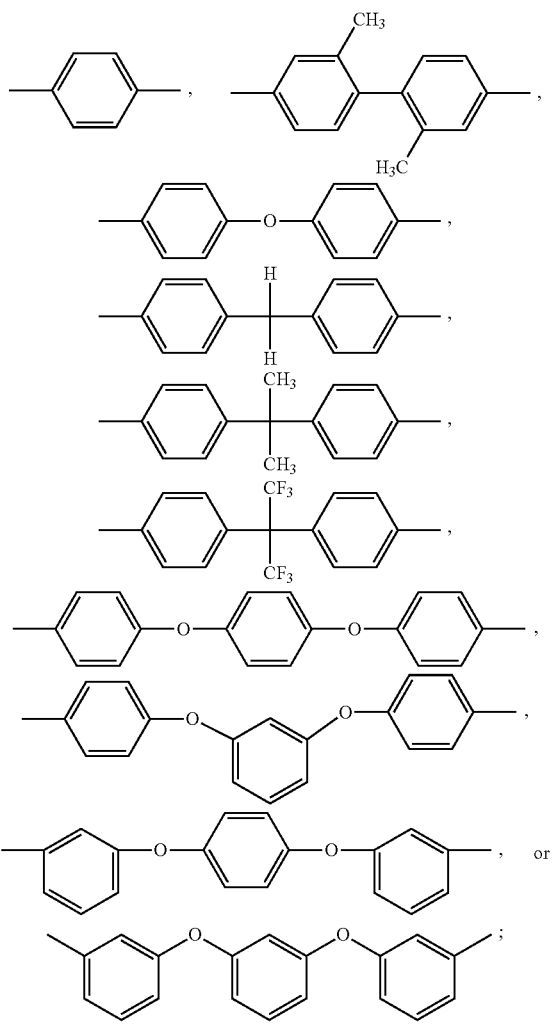

and
(v) an aprotic polar solvent, preferably said aprotic polar solvent is selected from the group consisting of dimethylformamide, dimethylacetamide, 1-methyl-2-pyrrolidinone and mixtures thereof, more preferably said aprotic polar solvent is selected from the group consisting of dimethylacetamide, 1-methyl-2-pyrrolidinone and mixtures thereof,
said solution comprising a molar ratio of said first monomer to combination of said second and third monomer of from about 0.8:1 to about 1.2:1, preferably said first monomer and combination of said second and third monomer are present in said solution in a molar ratio of from about 0.9:1 to about 1.1:1, more preferably said first monomer and combination of said second and third monomer are present in said solution in a molar ratio of from about 0.95:1 to about 1.05:1 and the total weight percent, based on total solution weight, of said first, second and third monomers is from about 2% to about 40%, preferably, the total weight percent, based on total solution weight, of said first, second and third monomers is from about 5% to about 35%, more preferably the total weight percent, based on total solution weight, of said first, second and third monomers is from about 10% to about 25%; to form a polymer in said solution;
b) precipitating said polymer out of said solution, preferably said precipitating comprises by combining said solution with a nonsolvent, preferably said solution is added to said nonsolvent, preferably said nonsolvent is selected from the group consisting of water, methanol, ethanol, 2-propanol and mixtures thereof; and
c) removing the precipitated polymer from said combination of solution and non-solvent.

Applicants disclose a process according to Paragraph 0030 wherein said third monomer is present in said solution in a molar ratio of said second monomer to third monomer of from about 0.001:0.999 to about 0.999:0.001, preferably said third monomer is present in said solution in a molar ratio of said second monomer to third monomer of from about 0.01:0.99 to about 0.99:0.01, more said third monomer is present in said solution in a molar ratio of said second monomer to third monomer of from about 0.1:0.9 to about 1:1.

Applicants disclose a process according to Paragraphs 0030 wherein:
a) said thermally imidizing comprises heating said solution to within a temperature that is from 50° C. below said solution's boiling point to said solution's boiling point, preferably said thermally imidizing comprises heating said solution to within a temperature that is from 20° C. below said solution's boiling point to said solution's boiling point and holding said solution at said temperature for about three hours to about 24 hours, preferably said solution is held at said temperature for about 8 hours to about 24 hours, more preferably said solution is held at said temperature for about 12 hours to about 24 hours; and preferably an azeotropic agent is added to said solution before or during heating said solution, more preferably said azeotropic agent is added to said solution before heating, preferably said azeotropic agent is selected from the group consisting of toluene, xylene and mixtures thereof; and
b) said chemical imidizing comprises adding a dehydrating agent and a base to said solution, preferably said dehydrating agent is selected from the group consisting of acetic anhydride, trifluoroacetic anhydride and mixtures thereof, and preferably said base is selected from the group consisting of pyridine, trimethylamine,2-picoline and mixtures thereof; and holding said solution at a temperature of from about 0° C. to about 120° C. for at said temperature for about three hours to about 48 hours, preferably said solution is held at said temperature for about 12 hours to about 24 hours, more preferably said solution is held at said temperature for about 18 hours to about 24 hours.

Figure 1B:
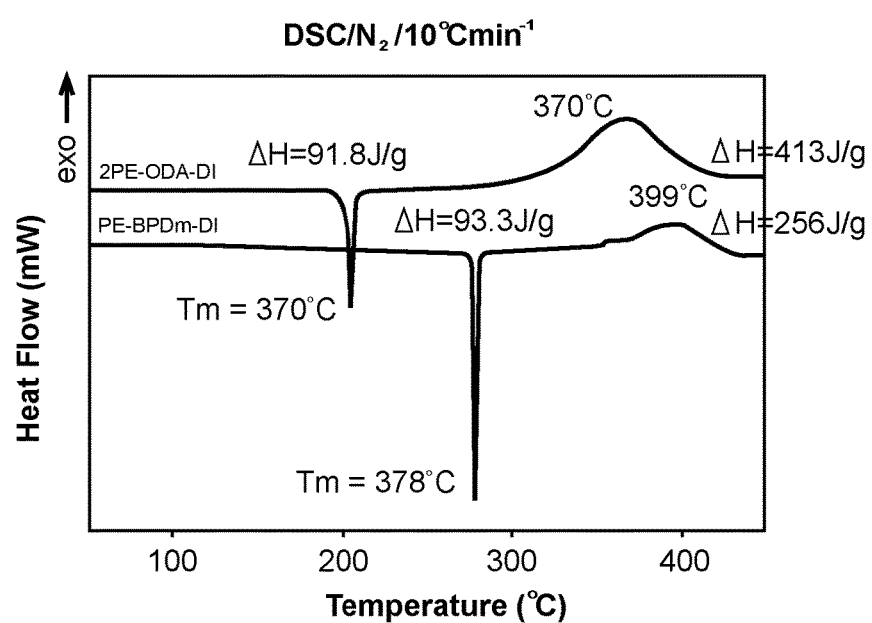
FIG. 1B depicts a composite of DSC thermograms for FIG. 1A

Thermal Chemistry of Phenylethynyl Group. Connell, Smith, and Hergenrother, ("Oligomers and polymers containing phenylethynyl groups." Journal of Macromolecular Science, Reviews in Macromolecular Chemistry and Physics 2000, C40, 207-230), Applicants believe that this article teaches that the mono-phenylethynyl (PE)-functionalized groups, regardless of their location in polymeric materials, i.e. whether being attached to the chain-ends or side-chains of a linear oligomer or polymer, are chemically dormant up to 300° C. Using the onset temperature of thermally-induced reaction of PE groups as the reference point, this notion has been verified by the synthesis, FIG. 1A, and differential scanning caloriemetry (DSC) experiments of the di-phthalimide (DI)-endcapped model compounds derived from the diamine, (3,5-diaminophenyl) (4-(phenylethynyl)benzophenone (PE-BPDAm) with a single PE pendants, and our claimed diamine, 4,4'-oxybis(3-(phenylethynyl) aniline) (2PE-ODA) with two PE pendants, FIG. 1B. The m.p. of PE-BPDm-DI is 278° C. and the onset of PE thermal reaction is ca. 350° C., and, for 2PE-ODA-DI, they are 267° C. and 300° C., respectively.

Monomer Compositions and Method of Synthesis. The molecular structures of the multi-phenylethynylated diamine monomers, viz. diphenylethynyl (2PE)-, diphenylethynyl (3PE)-, and diphenylethynyl (4PE)-containing oxy-dianiline (ODA) and methylene-dianilne (MDA are depicted as follows:

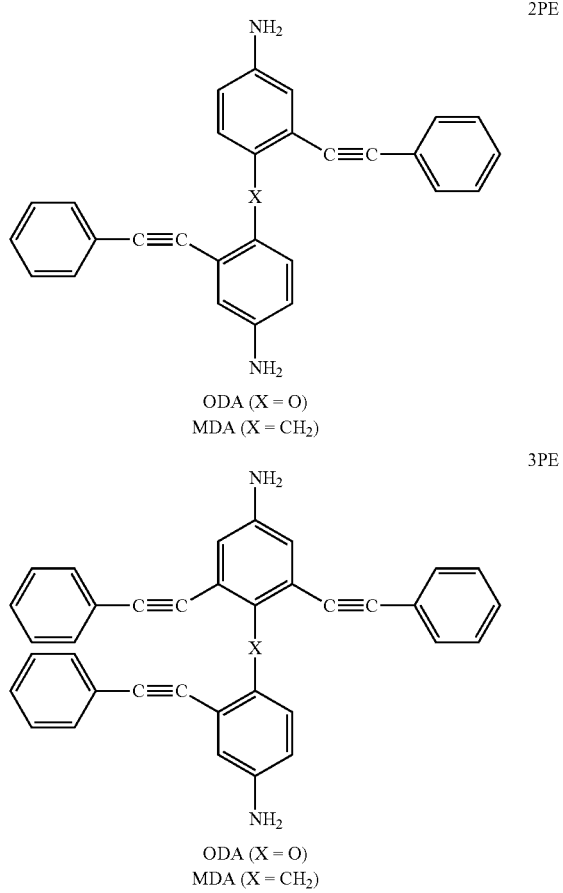

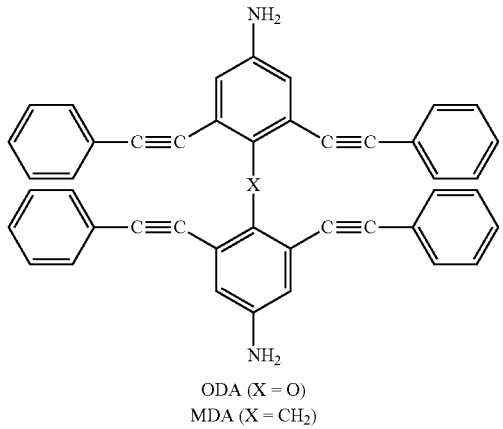

Figure 2:
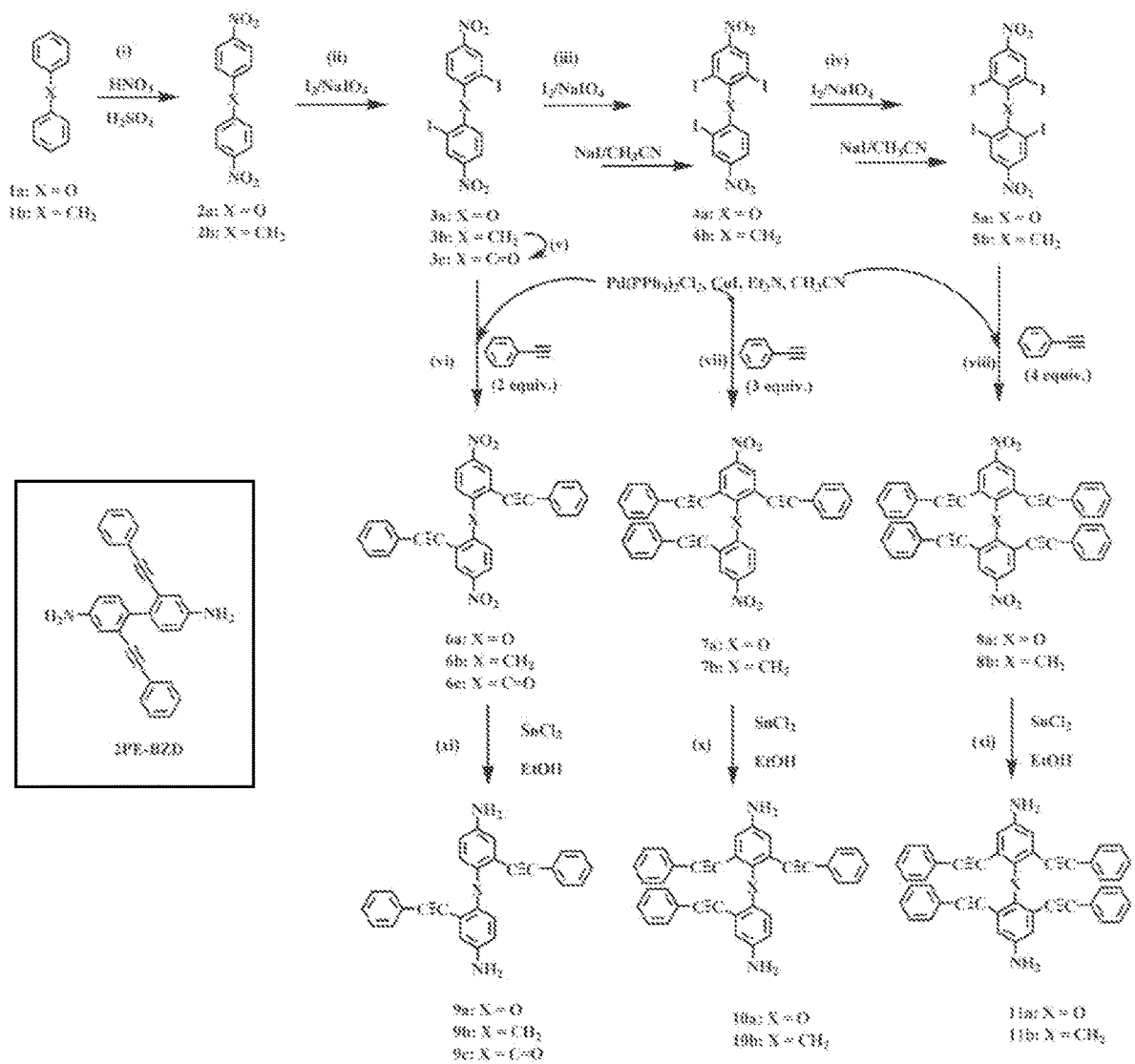
FIG. 2 depicts the linear and parallel synthesis sequences for the bis(aniline) monomers containing bis(phenylethynyl), tris(phenylethynyl), and tetrakis(phenylethynyl) groups.

Referring to FIG. 2, starting from diphenyl ether or diphenylmethane, the general synthesis of multiple-phenylethynylated bis(aniline) compounds that are para-linked to a simple ortho- or para-directing X-group, namely either $CH_2$ or O are conducted using the following types of organic synthetic reactions: (a) nitration, step (i); (b) aromatic/oxidative iodination, steps (ii)-(iv); Cu/Pd-catalyzed arylethynyl (Sonogashira) coupling reaction, steps (v)-(vi); (c) chemical reduction of nitro group.

Figure 3:
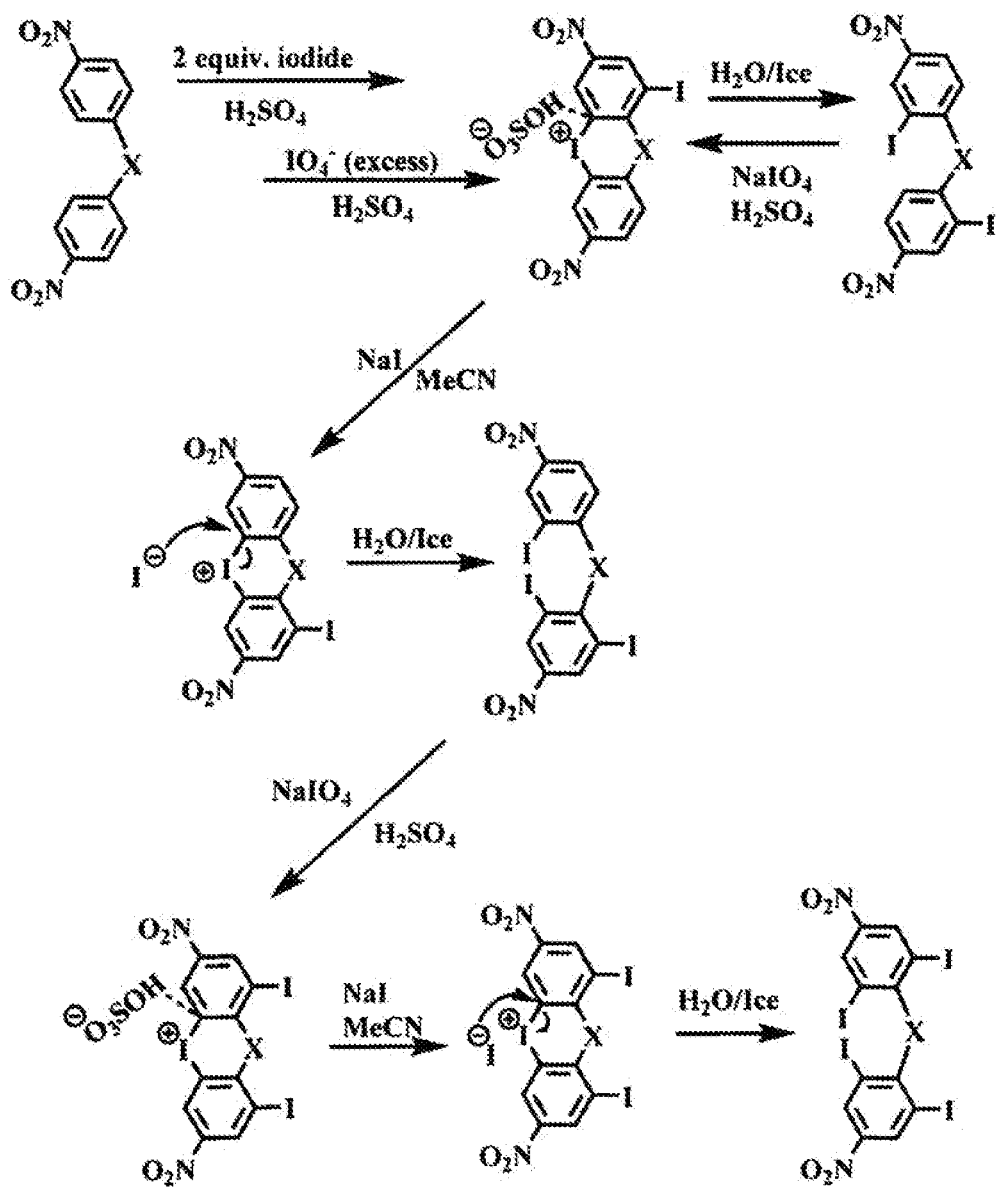
FIG. 3 depicts the linear synthesis of di-iodo, tri-iodo and tetra-iodo intermediates via repeating oxidative iodination reaction.

Referring to FIG. 3, the key precursors to these diamines are the halogenated bis(4-nitrobenzene) compounds. The iodinated bis(4-nitrobenzene) compounds, are preferred precursors in order to counter the steric hindrance inherent at the ortho positions during the Cu/Pd-catalyzed aryl-ethynyl coupling reaction because of the higher reactivity of aryl iodide than aryl bromide. In addition, because of the deactivation of the nitro groups, stronger oxidizing conditions using periodic acid ($HIO_4$) in addition to $I_2$ were required. Applicants believe that the following article L. Kraszkiewicz, et al. *Synthesis* 2006, 1195-1199, teaches that periodic acid is typically generated in situ by mixing the stable alkali (meta) periodate (e.g. $NaIO_4$) and concentrated sulfuric acid. When iodine ($I_2$) or iodide (from NaI or KI) is mixed with periodic acid in appropriate ratio (e.g. iodide: periodate=1: 3), a strong electrophile, formally iodonium ($I^+$), that is capable to engage in electrophilic substitution reaction with even strongly deactivated arene (for example, by the presence of nitro group) is generated. This one-pot oxidative iodination procedure was applicable to the synthesis of the di-iodo-bis(4-nitrobenzene) compounds directly from the bis(4-nitrobenzene) starting materials. However, for the synthesis of tri- and tetra-iodo-bis(4-nitrobenzene) compounds, the one-pot procedure did not yield the desired products (see Comparative Examples 1 and 2). Applicants believe that it is known that diaryliodonium compounds (see V. V. Grushin, *Chemical Society Reviews* 2000, 29, 315-324) can be converted to aryl iodides efficiently using iodide salts under mild conditions (see B. Hu et al, *Chemistry-A European Journal* 2015, 21, 6394-6398.) Therefore, a two-step oxidative iodination involving the (i) isolation of the diaryiodonium intermediates, followed by (ii) the treatment with sodium iodide was used. In polar solvent such as acetonitrile, formally a tandem sequence of (ii-a) counter-ion exchange and (ii-b) aromatic nucleophilic substitution (ArSN) at the ipso position by the iodide counter-anion. With the original aryliodonium moiety becoming aryliodide, the di-iodide arene product is resulted.

Finally and referring to FIG. 2 again, in the aryl-ethynyl coupling reaction, there was an initial problem with Pd catalysis that resulted in mainly de-iodinated and cycloaddition side-products. The combined palladium-copper (Sonogashira) catalysis (in steps v-vii) helped to circumvent the problem. The final reaction (in steps ix-xi, FIG. 2) requires the reduction of the two nitro groups in the presence of 2 phenylethynyl groups and the use of stannous chloride in ethanol as reducing system had worked out well.

Figure 4:
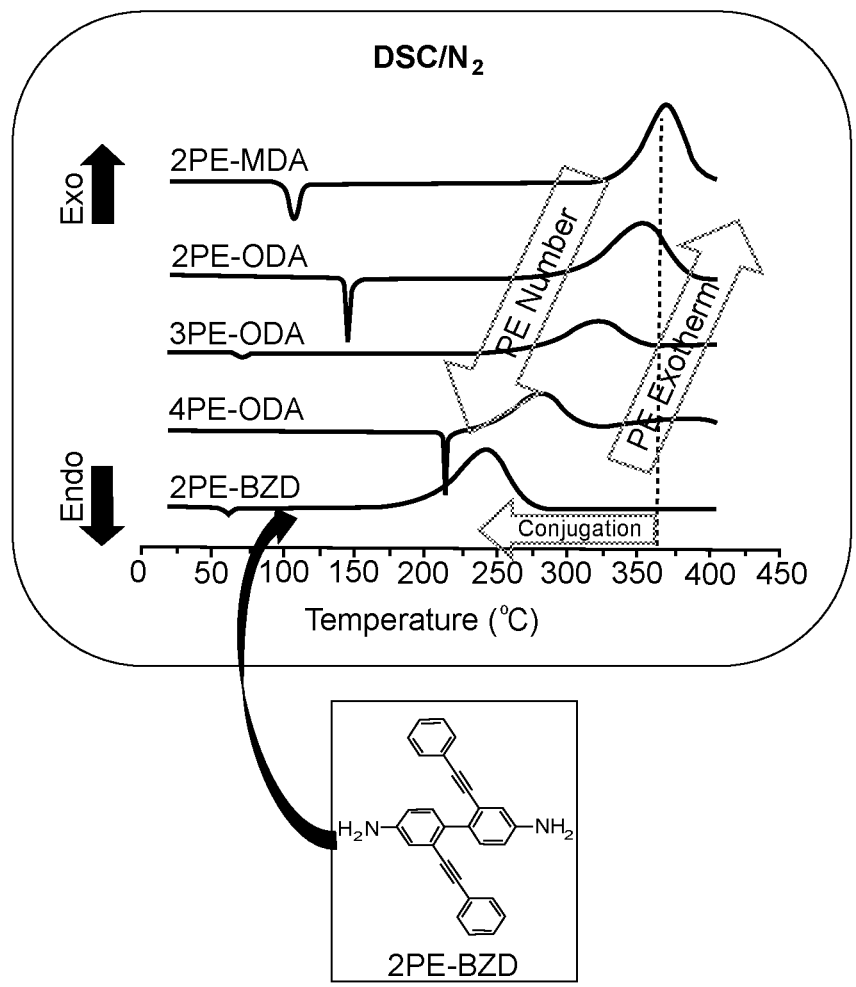
FIG. 4 depicts comparative plots of DSC scans of 2PE-containing methylenedianiline (2PE.ODA) and oxydianiline (2PE.ODA), 3PE-containing and 4PE-containing oxydianiline, and 2PE-containing benzidine (2PE.BZD).

Thermal Properties: Thermal properties of the multiple phenylethynylated diamines were characterized by differential scanning calorimetry (DSC) that was conducted under nitrogen atmosphere, from 25° C. to 400° C., and at the scanning rate of 10° C./min. Referring to FIG. 4, the composite plots of DSC results for 4,4'-oxybis(3-(phenylethynyl) aniline), 2PE.ODA (9a); 4,4'-methylenebis(3-(phenylethynyl) aniline), 2PE.DMA (9b); 4,4'-methylenebis(3-(phenylethynyl) aniline), 3PE.ODA (10a); 4,4'-oxybis(3,5-bis(phenylethynyl) aniline), 4PE.ODA (11a) and 2,2'-bis(phenylethynyl)benzidine, 2PE.BZD (FIG. 4 inset) are depicted. 2PE.BZD is included for comparison because of the conjugation and proximity of the PE groups located at two different benzene rings. This is in contrast to 2PE.ODA and 2PE.MDA whose two PE group are not conjugated because of the presence of an ether or a methylene separator, albeit still being in favorable proximity for a thermal pericyclic reaction due to the tetrahedral geometry of the ether oxygen and $CH_2$ units, hence angular linkages. However, the onset temperatures for 2PE.ODA, 3PE.ODA and 4PE.ODA are clearly higher than that for 2PE.BZD. The direct comparison of 2PE.ODA and 2PE.BZD suggests that conjugation effect lowers the reaction temperature and promote intramolecular pericyclic reaction. It is also noted that (i) within the MPA.ODA series, the trend for both the onset and peak temperatures is influenced by the number of PE moieties: 2PE>3PE>4PE; (ii) the occurrence of intermolecular reaction, i.e. crosslinking is likely as indicated by a smaller exotherm observed at temperatures >350° C. for 4PE.ODA. With respect to processing window for the respective PE materials that may be projected from the $\Delta(T_{onset}-T_m)$ in Table 1 below, 2PE- or 3PE-based materials are better than 4PE-based materials. However, because of the low $T_{onset}$ (221° C.), it may find uses as polymerization initiator for the phenylethynyl-terminated thermosetting oligomers that requires curing temperatures well above 350° C.

TABLE 1

Thermal properties of multiple phenylethynylated diamines determined by DSC in $N_2$ at scanning rate of 10° C./min

| Monomer | Mp (° C.) | $T_{onset}$ (° C.) | $T_{peak}$ (° C.) | $\Delta(T_{onset} - T_m)$ (° C.) | Rxn Enthalpy (J/g) | Rxn Enthalpy (kJ/mol) |
|---|---|---|---|---|---|---|
| 2PE.BZD | 62.0 | 160 | 243 | 98 | 865 | 333 |
| 2PE.ODA | 145 | 238 | 352 | 93 | 746 | 299 |
| 2PE.MDA | 108 | 311 | 370 | 193 | 656 | 261 |
| 3PE.ODA | 71.0 | 238 | 321 | 167 | 500 | 250 |
| 4PE.ODA | 214 | 221 | 281 | 7 | 520 | 312 |

An example of a cross-linkable thermoplastic that is either a linear homopolyimide or a linear copolyimide containing multiple arylethynyl pendants in a repeat unit has the following structure:

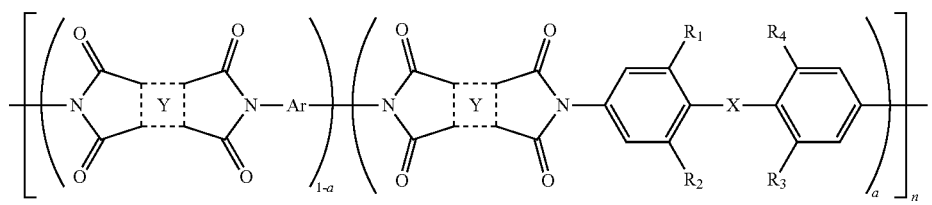

wherein
a) each X is independently O, $CH_2$, or C=O;
b) $R_1$, $R_2$, $R_3$, and $R_4$ are each independently H or phenylethynyl;
c) each Y is selected from one of the following moieties:

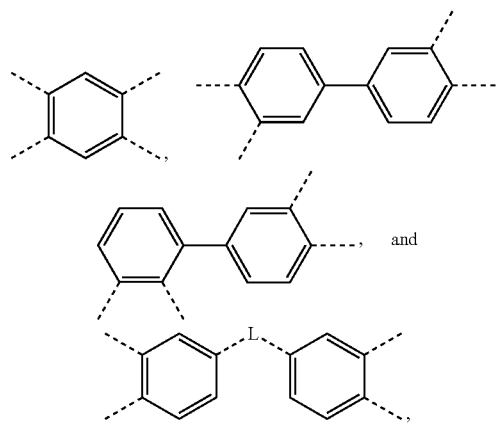

where L is a bivalent linker selected from the one of following moieties: O, C=O, $SO_2$, $C(CF_3)_2$, $C(CF_3)Ph$, and $—O-(pC_6H_4)—C(CF_3)_2-(pC_6H_4)—O—$;
d) each a is from about 0.01 to about 1, preferably a is from about 0.05 to about 1, more preferably a is from about 0.1 to about 1; and
e) n is an integer from about 3 to about 200, preferably n is an integer from about 5 to about 100, more preferably n is an integer from about 5 to about 50.

Because of the temperature sensitivity of the multi-phenylethynyl (xPE) group as discussed in the foregoing paragraphs, and the relatively high-temperature requirement (generally greater than 200° C.) for thermal imidization of the poly(amic acid) precursor (PAA) that is initially formed from the polycondensation reaction of a dianhydride and a diamine, chemical imidization of xPE-containing PAA that can be effected at significantly lower temperatures (generally from room temperature to 50-70° C.) is preferred. Typically, acetic anhydride in conjugation with trimethylamine or pyridine is used as the cyclodehydrating/imidizing agent. As a representative examples for the synthesis of this new family of xPE-containing, thermoplastic and crosslinkable homopolyimides and copolyimides, the generic scheme for the polycondensation of (i) a 2PE-containing diamine and a dianhydride; and (ii) a 2PE-containing diamine, 4,4'-oxydianile (ODA), and 4,4'-oxy (diphthalic anhydride) is depicted in FIG. 5 and FIG. 6, respectively.

Figure 5:
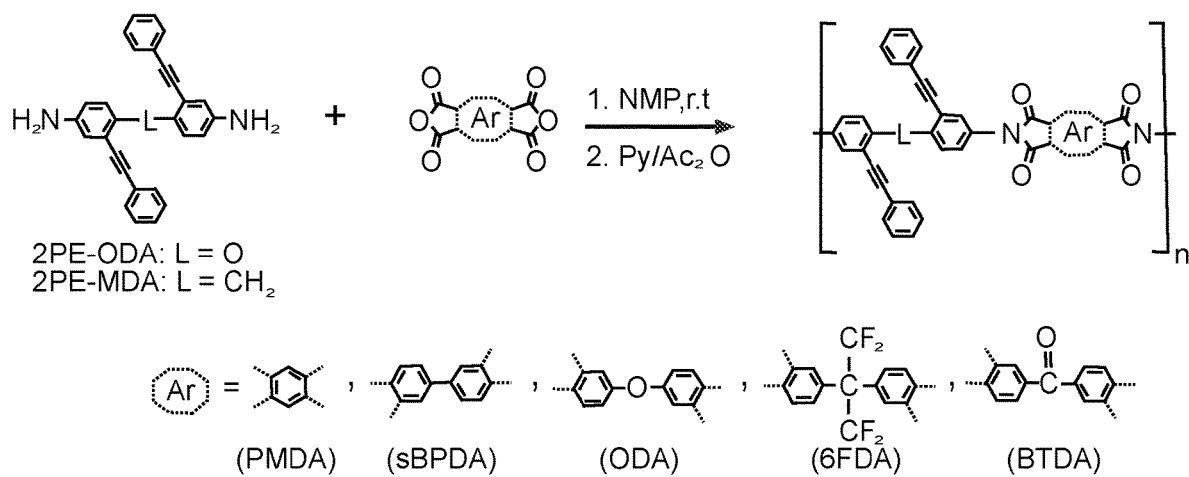
FIG. 5 depicts the synthesis of homopolyimides containing 2-4 phenylethynyl groups per repeat unit as exemplified by the polycondensation of 2PE-ODA or 2PE-MDA with 5 common dianhydrides: PMDA, s-BPDA, ODPA, 6FDA and BTDA.

Referring to FIG. 5, 2PE.ODA and 2PE.MDA were selected as examples to illustrate the generality of such "chemical imidization" synthesis for the multi-PE-containing homopolyimides, to polymerize with 5 common dianhydrides: PMDA, sBPDA, ODA, 6FDA and BTDA. In a one-pot fashion, stoichiometric amount of 2a PE-diamine and a dianhydride were mixed in NMP at room temperature for a period of time to generate the corresponding poly(amic acid), and dehydrating/imidizing agent such as a mixture of acetic anhydride and pyridine was added in excess. The resulting solution was stirred at room temperature for 24 hr. to ensure complete conversion of poly(amic acid) to polyimide.

Figure 6:
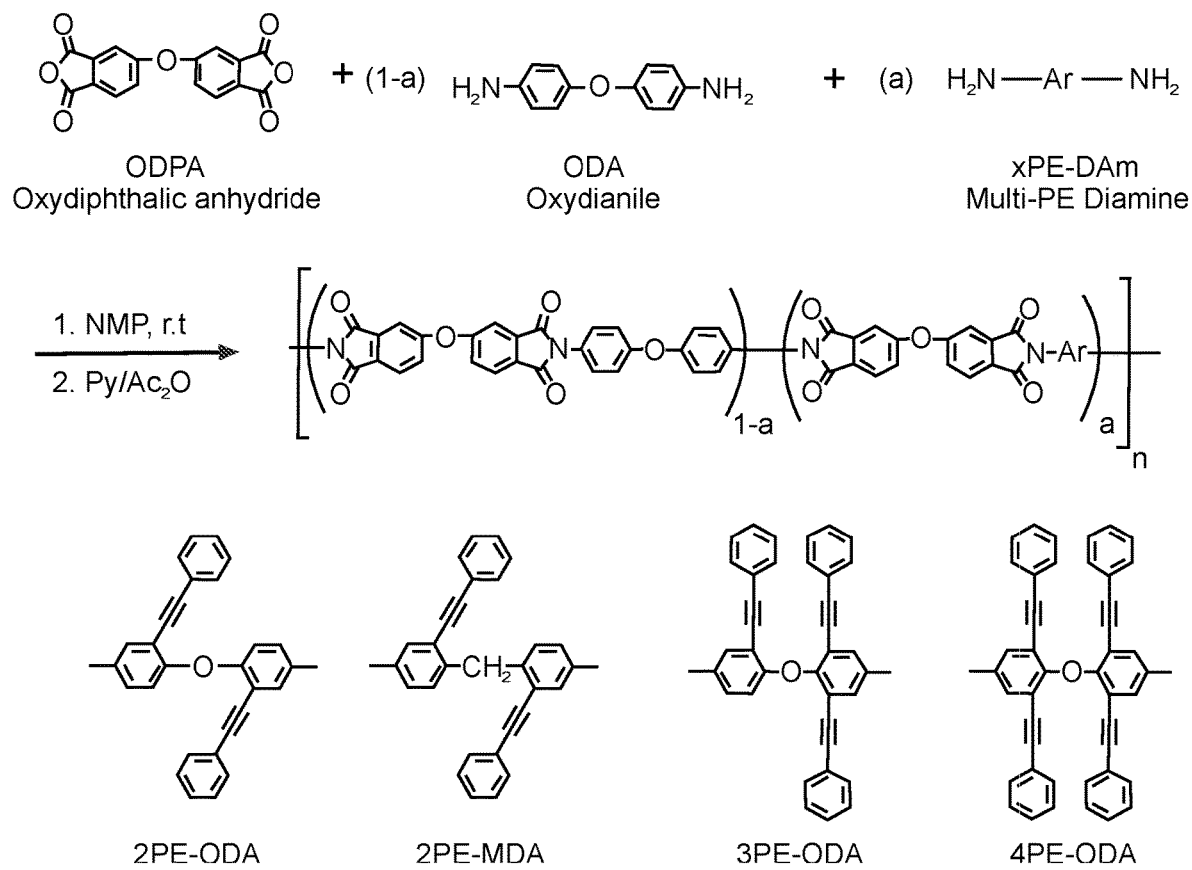
FIG. 6 depicts a generic synthesis of co-polyimides containing 2-4 phenylethynyl groups per repeat unit as exemplified by the polycondensation of xPE-diamines with ODA and ODPA.

Referring to FIG. 6, 2PE.ODA and 2PE.MDA were selected as examples to illustrate the generality of synthesis for the multi-PE-containing co-polyimides, to polymerize with oxy-4,4'-dianiline (ODA) and oxy-4,4'-di(phthalic anhydride) (OPDA). It is understood that the range of co-polyimide compositions cover all the combinations of an xPE-containing diamine (e.g. 2PE-ODA, 2PE-MDA, 3PE-ODA, 4PE-ODA, etc.), a non-PE diamine (e.g. ODA) and a dianhydride (e.g. OPDA).

Thermal properties of linear co-polyimides containing multiple PE pendants are characterized by differential scanning calorimetry (DSC) to quantify their thermal behaviors in terms of initial and cured glass-transition temperatures, the onset and peak temperatures of the exotherms due to the thermally-induced crosslinking of PE groups.

Figure 7:
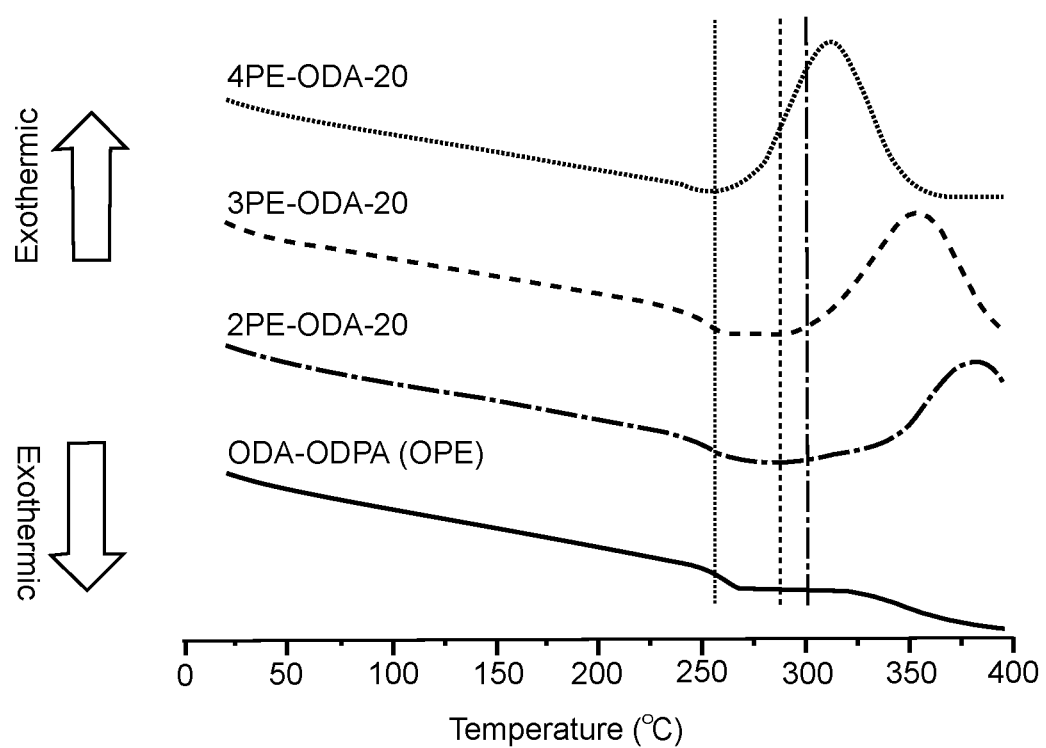
FIG. 7 depicts thermal reactivity of PE pendants as indicated by the onset temperatures of the PE reaction exotherms for ODA-ODPA (OPE) homopolymer, and copolyimides of ODA, ODPA and xPE-ODA (x=2-4), which was set at 20 mol %. Increments in the PE-substitution on ODA lead to lower onset temperature and lower peak curing temperature. Higher effective concentration [PE], or "number-proximity" lead to lower kinetic barrier of thermally-induced crosslinking reaction.

Referring to FIG. 7, the effects of number and proximity of PE within a repeat unit on the PE curing exotherm for the samples containing 20 mol % of xPE moieties (x=2,3,4) in the copolyimides and 0 mol % in the homopolymer, ODA-ODPA (OPE) are revealed by DSC experiments. Increase in the PE-substitution on ODA leads to lower onset temperature and lower peak curing temperature. This is likely because higher effective [PE] or "number-proximity" effect promotes intramolecular thermal reaction with lower kinetic barrier, and kicks off the ensuing crosslinking reactions.

Figure 8:
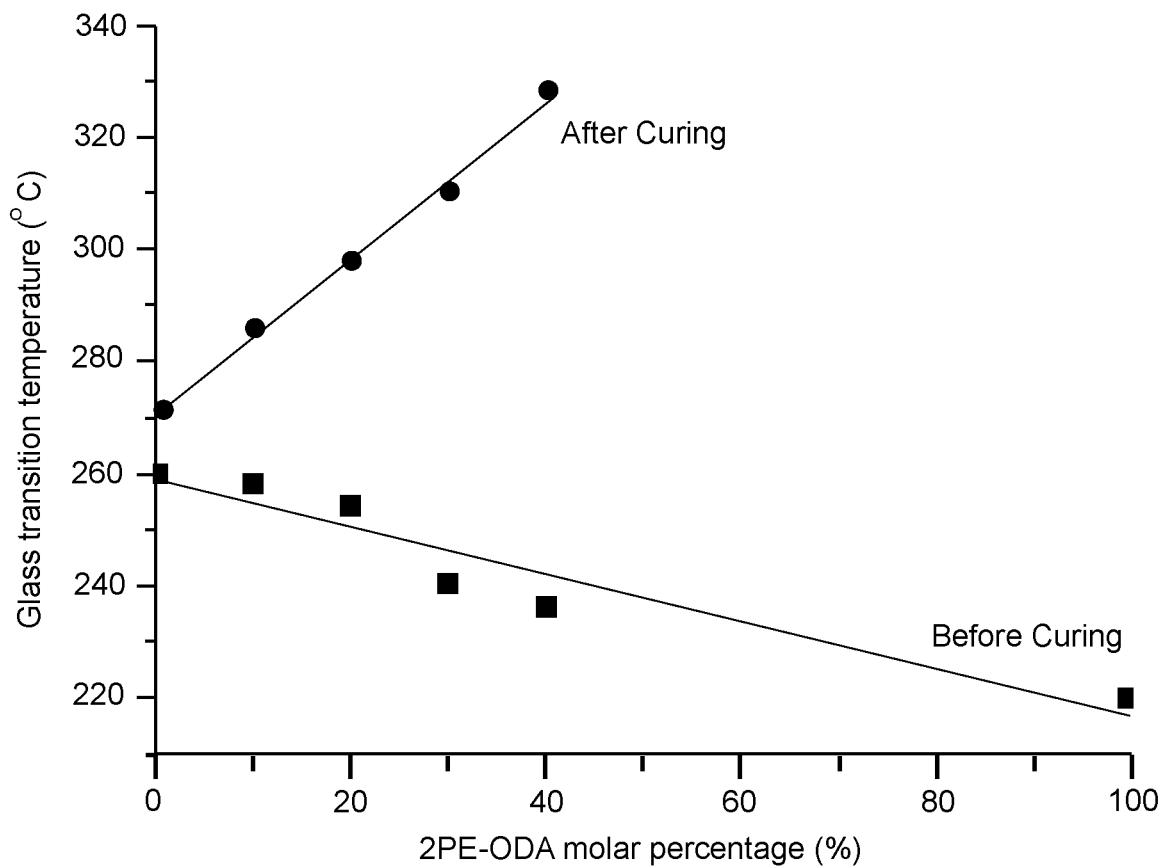
FIG. 8 depicts the composite plot of glass-transition temperatures before ($T_{g.ini}$) and after ($T_{g.cure}$) PE curing vs. 2PE-ODA content. Both $T_{g.ini}$ and $T_{g.cure}$ are linearly dependent on the 2PE.ODA content.

Referring to FIG. 8, the linear relationships of both initial ($T_{g.ini}$) and cured ($T_{g.cure}$) glass-transition temperatures with the 2PE.ODA content are depicted graphically for the copolymers derived from oxy-4,4'-diphthalic anhydride, oxy-4,4'-dianilne and 2PE.ODA. The $T_{g.ini}$ value decreases as the molar content of 2PE.ODA increases because of the decrease in chain-chain interactions hindered by the bulky PE pendants. The $T_{g.cure}$ value increases as the molar content of PE groups increases because of the increase in crosslinking density. The increasing trend in $T_{g.cure}$ is apparently steeper than the decreasing slope of $T_{g.ini}$ values.

Figure 9:
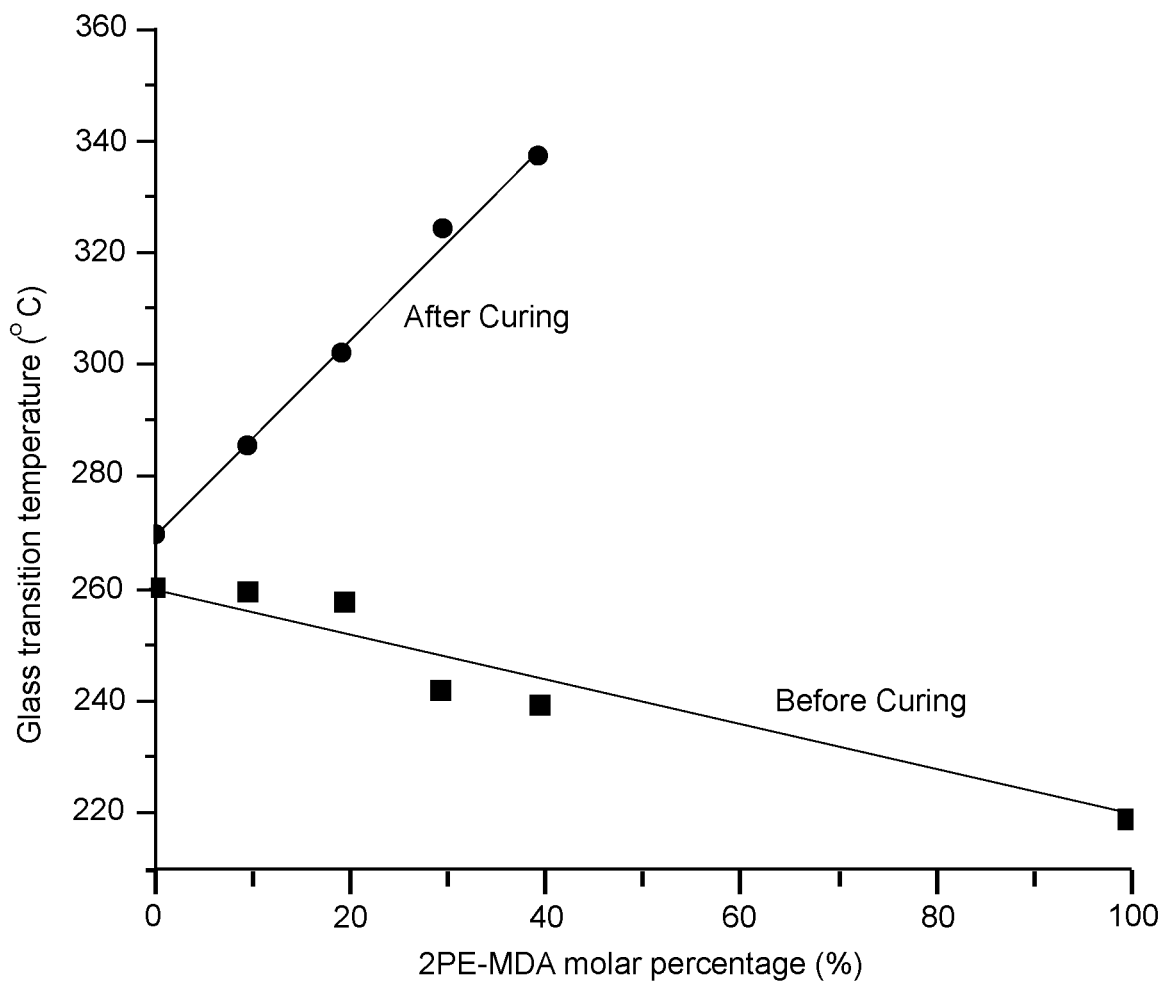
FIG. 9 depicts the composite plot of glass-transition temperatures before ($T_{g.ini}$) and after ($T_{g.cure}$) PE curing vs. 2PE-ODA content. Both $T_{g.ini}$ and $T_{g.cure}$ are linearly dependent on the 2PE.MDA content.

Referring to FIG. 9, the linear relationships of both initial ($T_{g.ini}$) and cured ($T_{g.cure}$) glass-transition temperatures with the 2PE.MDA content are depicted graphically for the copolymers derived from oxy-4,4'-diphthalic anhydride, oxy-4,4'-dianilne and 2PE.MDA. Both $T_{g.ini}$ and $T_{g.cure}$ trends are similar to those observed from the copolymers derived from 4,4'-oxy-diphthalic anhydride, oxydianilne and 2PE.ODA.

The two most common techniques used for AM are fused filament fabrication (FFF), which is also known as fused deposition modeling (FDM), and selective laser sintering (SLS). FFF generally requires the polymer to be in the form of a tightly controlled filament with a typical diameter of 1.75 mm (+0.25 mm), while SLS generally requires the polymer to be in the form of a uniform size distribution fine powder. While the focus of embodiments of the present invention described herein is on FFF and SLS, e.g., making a filament of previously un-extrudable high crosslink density thermosetting polyimides and allowing SLS on powders that behave similar to conventional thermoplastic materials such as Ultem® or polyether-ether ketone (PEEK) when melt-processed with a laser, the application of the composition and materials is not limited thereto.

Thus, in accordance with an embodiment of the present invention an additive manufacturing process for preparing a three dimensional article is provided. The method may include one or more of the following steps: forming a phenylethynyl-functionalized polyimide material; partially curing the phenylethynyl-functionalized polyimide material to a degree of curing that is in a range from about 5 percent to about 30 percent; depositing a plurality of layers comprising the partially-cured phenylethynyl-functionalized polyimide material to form a 3D article; and heating the 3D article to a temperature up to, but not exceeding, a first glass transition temperature and maintaining the temperature for a sufficient time to advance the degree of curing.

Test Method

For purposes of the present application, average particle size and particle size distribution are taken at a Dv50 using a Mastersizer 3000 laser diffraction particle size analyzer. Mastersizer 3000 laser diffraction particle size analyzers can be obtained from Malvern Panalytical Inc. of Westborough MA 01581-1042 United States. The Mastersizer 3000 should be used in accordance with the instrument's instruction manual as supplied by Malvern Panalytical Inc. to obtain average particle size and particle size distribution at a Dv50.

Examples

The following examples and methods are presented as illustrative of the present invention or methods of carrying out the invention, and are not restrictive or limiting of the scope of the invention in any manner.

Example 1-Synthesis of 4,4'-oxybis(3-(phenylethynyl) aniline), 2PE.ODA
(a) 2,2'-diiodo-4,4'-dinitrodiphenyl ether. To a 1 L three necked flask, equipped with mechanical stir, 400 mL 95-98% sulfuric acid and 10.76 g (50.5 mmol) sodium periodate were charged. To the suspension, 25.15 g (151.5 mmol) potassium iodide was added within 1 hour. The mixture was stirred at room temperature for additional 1 hour. This mixture was slowly added to a suspension of 26.02 g (0.100 mol) 4,4'-dinitrodiphenylether suspension in 200 mL 95% sulfuric acid within one hour. The mixture was stirred for 3 hours, then, poured into ice water. The precipitate was collected via filtration, washed several times with water, then 300 mL ethanol, air flower dried to afford crude product. The crude product was further purified by recrystallization from toluene/heptane mixture. Two crops of crystals were harvest. 27.2 grams of crystals were harvested as the first crop of product, m.p. 171.6-174.6° C., 53% isolated yield. 10.7 grams of crystals were harvested as the second crop of product, m.p. 170.5-171.5° C., 27.7% additional isolated yield. $^1$H NMR (400 MHZ, CDCl$_3$) δ=8.02-8.08 (d, J=4.8 Hz, 2H), 8.23-8.26 (dd, J=4.8, 8.8 Hz, 2H), 6.90-6.92 (d, J=8.8 Hz, 2H). Elemental analysis calculated for C$_{12}$H$_6$I$_2$N$_2$O$_5$, C, 28.15; H, 1.18; N, 5.47; O, 15.62. Found: C, 28.06; H, 1.14; N, 5.16; 0, 15.78.

(b) 2,2'-bis(phenylethynyl)-4,4'-dinitrodiphenylether. To a 500 mL round bottom flask, equipped with stir bar, and nitrogen inlet, 25.60 g (50.0 mmol) 2,2'-diiodo-4, 4'-dinitrodiphenylether, 47.6 mg (0.250 mmol) copper iodide and 350.9 mg (0.500 mmol) Bis(triphenylphosphine) palladium chloride were charged. After vacuum and backed fill with nitrogen for three times, 20.43 g (200 mmol) phenylacetylene, 25 ml trimethylamine and 100 mL acetonitrile were charged. The mixture was stirred at room temperature for 4 hours, then, organic solvents were removed under vacuum. Solids were washed with water, 90 mL ethanol for three times, then air dried. The solids were dissolved in hot toluene, 2 grams activated carbon black was added, then filtrated. The product was further purified by recrystallization from toluene twice to give 15.38 grams of product as light yellow crystals, m.p. 180.5-181.9° C., 66.7% isolated yield. Additional 1.05 grams (m.p. 178.7-180.7° C., 4.6% additional isolated yield) was obtained as second crop of product. $^1$H NMR (400 MHZ, CDCl$_3$) δ=8.49-8.50 (d, J=2.8 Hz, 2H), 8.18-8.21 (dd, J=2.8, 8.8 Hz, 2H), 7.30-7.42 (m, 10H), 7.09-7.11 (d, J=8.8 Hz, 2H). Elemental analysis calculated for C$_{28}$H$_{16}$N$_2$O$_5$, C, 73.04; H, 3.50; N, 6.08; O, 17.37. Found: C, 73.03; H, 3.47; N, 6.20; O, 17.33.

(c) 4,4'-oxybis(3-(phenylethynyl) aniline) (2PE.ODA). To a 300 mL round bottom flask, equipped with nitrogen inlet, stir bar, and condenser, 15.19 g (30.00 mmol) 2,2'-bis(phenylethynyl)-4,4'-dinitrodiphenylether and 44.66 g (198.00 mmol) Tin (II) chloride were charged. After vacuum and backed filled with nitrogen for three times, 150 mL ethanol was added. The mixture was heated to 80° C., and held for 3 hours. After cooled to room temperature, ethanol was removed under vacuum, then the residual poured into a solution of 31.68 grams of sodium hydroxide in 620 mL water. The mixture was stirred for 30 minutes, and extracted with 200 mL ethyl acetate each time for 3 times. The combined organic solution was washed with de-ionized water, for three times, then dried over anhydrous sodium sulfate. The organic solution was filtered through a plug of silica gel, then, concentrated under vacuum to give crude product as yellowish viscous oil. The oil as further purified further purified by recrystallization from toluene three times.4.18 g of final product was obtained as slightly yellow crystals, m.p. 141.7-142.7° C., 31.6% isolated yield. $^1$H NMR (400 MHZ, CDCl$_3$) δ=7.43-7.45 (m, 4H), 7.24-7.26 (m, 6H), 6.88 (d, J=2.8 Hz, 2H), 6.76-6.79 (d, J=8.8 Hz, 2H), 6.58-6.61 (dd, J=2.8, 8.8 Hz, 2H), 3.52 (broad, 4H). IR (cm$^{-1}$): 3433, 3412, 3355, 3330, 3211, 2208, 1607, 1496, 1480, 1435, 1261, 1218, 856, 818, 753, 687, 593, 531, 462. Elemental analysis calculated for C$_{28}$H$_{20}$N$_2$O, % C, 83.98; % H, 5.03; % N, 7.00; % O, 4.00. Found: % C, 83.63; H, 4.98; N, 6.95; O, 4.05. ESI-MS: m/z 401.2 [(M+H)$^+$].

Example 2-4,4'-methylenebis(3-(phenylethynyl) aniline) (2PE.MDA)

(a) 4,4'-dinitrodiphenymethane: To a 1000 mL three necked round bottom flask equipped with a stir bar and a thermometer, 102 mL concentrated sulfuric acid was added and cooled by ice-water bath. 70% Nitric acid (114 mL) was charged slowly. The mixture was cooled by ice-water bath to about 5° C. To the nitrating mixture, diphenylmethane (30.28 g, 0.18 mol) dissolved in 70 mL acetic acid was added at such a rate that the temperature is kept below 10° C. After addition of diphenylmethane/AcOH solution, the reaction mixture was stirred in an ice-water bath for 2 hours, and then poured into 600 g ice in a large beaker. The crude product was collected on a filter funnel, washed with de-ionized water (3×), ethanol (3×), times, and finally air dried. The crude product was purified by recrystallization from toluene to give near-white crystals. 15.82 grams of product was obtained, 34.0% isolated yield, m.p. 182.5-185.0° C. $^1$H NMR (400 MHZ, CDCl$_3$) δ=8.18 (d, J=8.5 Hz, 4H), 7.35 (d, J=8.4 Hz, 4H), 4.19 (s, 2H).

(b) 2,2'-diiodo-4,4'-dinitrodiphenylmethane: To a 1000 mL round bottom flask equipped with a stir bar, 98% concentrated sulfuric acid (360 mL) and sodium periodate (NaIO$_4$, 9.68 g, 45.45 mmol) were charged. To the mixture, potassium iodide (KI, 22.63 g, 136.35 mmol) was added in small portion. After KI addition, the mixture was further stirred for half hour to form a dark brown solution. The resulting iodinating reagent in the form of the dark brown solution was added to a suspension of 4,4'-dinitrodiphenylmethane (23.24 g, 90.00 mmol) in 140 mL concentrate sulfuric acid over 5 hours. After addition, the reaction mixture was stirred at room temperature for additional 20 hours. The mixture was poured into 1000 g ice in a large beaker, and precipitated crude product was collected on a filter funnel. The crude solids were washed with copious amount of water, 5% aq. sodium bisulfite, water again, and finally air dried. The crude product was dissolved in ethyl acetate, and the insoluble particle was removed by filtration. The ethyl acetate filtrate was washed 3× with de-ionized water with the aid of a separatory funnel, and the dried over anhydrous sodium sulfate. After the removal of ethyl acetate by rotary evaporation, the crude product was obtained as slightly yellows solids. The crude product was further purified by recrystallization from toluene, to give 35.1 g product, m.p. 157.4-160.1° C., 76.4% isolated yield. $^1$H NMR (400 MHZ, CDCl$_3$): δ=8.74-8.75 (d, J=2.2 Hz, 2H), 8.15-8.17 (dd, J 8.4, 2.2 Hz, 2H), 7.07-7.09 (d, J=8.4 Hz, 2H), 4.31 (s, 2H). 13C NMR (101 MHz, CDCl$_3$): δ=148.3, 146.9, 134.6, 129.9, 123.5, 100.5, 51.8. Elemental analysis calculated for C$_{13}$H$_8$I$_2$N$_2$O$_4$, C, 30.61; H, 1.58; N, 5.49; O, 12.55. Found: C, 30.63; H, 1.54; N, 5.36; 0, 12.59.

(c) 2,2'-bis(phenylethynyl)-4,4'-dinitrodiphenylmethane To a 500 mL round bottom flask, equipped with a stir bar, and a nitrogen inlet, 2,2'-diiodo-4,4'-dinitrodiphenylmethane (35.70 g, 70.0 mmol), copper iodide (33.3 mg, 0.175 mmol) and bis(triphenylphosphine) palladium chloride (245.6 mg, 0.350 mmol) were charged. After three cycle of vacuuming and back-filling with nitrogen, phenylacetylene (28.56 g, 280 mmol), triethylamine (35 mL) and 140 mL acetonitrile were added. The mixture was stirred at room temperature for 4 hours, and then acetonitrile and excess phenylacetylene were removed under vacuum. Ethanol was added and the crude product was collected on a filter funnel, washed with 50 mL ethanol (6×), and then air dried. The crude solids were recrystallized from toluene to give 17.1 grams of product as light yellow crystals, m.p. 211.2-213.5° C., 53.3% isolated yield. $^1$H NMR (400 MHZ, CDCl$_3$): δ=8.43 (d, J=2 Hz, 2H), 8.09-8.11 (dd, J=8.8, 2.0 Hz, 2H), 7.47-7.49 (d, J=6.8 Hz, 4H), 7.32-7.38 (m, 8H), 4.67 (s, 2H). Elemental analysis calculated for C$_{29}$H$_{18}$N$_2$O$_4$, C, 75.97; H, 3.96; N, 6.11; 0, 13.96. Found: C, 75.96; H, 3.89; N, 6.10; 0, 13.94.

(d) 4,4'-methylenebis(3-(phenylethynyl) aniline) (2PE.MDA) To a 500 mL round bottom flask equipped with a stir bar, a condenser, and a nitrogen inlet, 2,2'-bis(phenyethynyl)-4,4'-dinitrodiphenylmethane16.0 g (35.0 mmol), Tin (ii) chloride (79.0, 0.35 mol) and 185 mL ethanol were charged. The mixture was heated in an oil bath temperature to 85° C. and held for 4 hours. After the mixture had been cooled to room temperature, ethanol was removed by rotary evaporation to give a viscous slurry. The slurry was poured into 550 mL of 10% potassium carbonate solution. The resulting mixture was filtered. The aqueous filtrate was extracted with 50 mL ethyl acetate for 3 times. The solid on the filter funnel was extracted with 200 mL ethyl acetate (5 times). The ethyl acetate extracts were combined, washed with 5% potassium carbonate solution followed by de-ionized water (2×), dried over sodium sulfate, and finally passed through a silica gel plug. After ethyl acetate had been removed on a rotary evaporator, the crude product was further purified by recrystallization from ethanol/water. 7.12 g of product was obtained as slight yellow needle like crystals, m.p 103.3-104.3° C., with a 51.5% isolated yield. $^1$H NMR (400 MHZ, CDCl$_3$): δ=7.44-7.46 (m, 4H), 7.25-7.26 (m, 6H), 6.95-6.97 (d, J=8.2 Hz, 2H), 6.85-6.86 (d, J=2.4 Hz, 2H), 6.53-6.55 (dd, J=8.2, 2.4 Hz, 2H), 4.30 (s, 2H), 3.53 (s, 4H). 13C NMR (101 MHz, CDCl$_3$): δ=144.2, 133.6, 131.5, 130.1, 128.2, 128.0, 123.5, 123.3, 118.2, 116.0, 92.7, 88.8, 36.6. IR (cm$^{-1}$): 3424, 3402, 3207, 3053, 3022, 2207, 1607, 1570, 1500, 1489, 1442, 1324, 1071, 888, 840, 823, 753, 687, 608, 458. Elemental analysis calculated for C$_{29}$H$_{22}$N$_2$, C, 87.41; H, 5.56; N, 7.03. Found: C, 87.49; H, 5.52; N, 7.04. ESI-Ms: m z 399.2 [(M+H)$^+$]

Example 3—General Polymerization Procedure (Chemical Imidization) for the synthesis of 2PE.ODA-DAn and 2PE.MDA-DAn (DAn=PMDA, sBPDA, ODA, 6FDA or BTDA) 1.00 mmol of 2PE-diamine (2PE.ODA or 2PE.MDA) was dissolved in 5 mL anhydrous dimethyacetamide (DMAc) or N-methyl-2-pyrrolidone (NMP), then, 1.00 mmol dianhydride (PMDA, sBPDA, ODA, 6FDA or BTDA) was added. The resulting of poly(amic acid) mixture was stirred at room temperature for 24 h, and then, diluted with 5 mL solvent, followed by the addition of a mixture of 2.0 mL acetic anhydride and 1.6 mL pyridine. The polymerization mixture was stirred at room temperature for additional 24 hours, and if it became difficult to stir, additional 5 mL NMP was added. The polyimide mixture was precipitated into 300 mL of 2-propanol, and filtered. The polyimide product was air dried, and then re-dissolved in 25 mL DMAc or NMP, followed by precipitation in 300 mL 2-propanol. The polyimide product was then collected on a filtration funnel, air dried, and finally dried in a vacuum oven at 0.5 torr, 130° C. for 24 hours. The yield of polyimide is generally quantitative.

Size Exclusion Chromatography was carried out using NMP containing 10 mM lithium bromide as eluent at 0.7 mL/min flow rate. Two Waters Styragel columns (HR-4E and HR-5E) in a serial were used as and maintained at 50° C. The columns were calibrated with narrow dispersion polystyrene samples. Molecular weight and polydisperse were obtained by conventional calibration. Differential calorimetric scanning (DSC; TA Instrument) was conducted under N$_2$ atmosphere and thermogravimetric analysis (TGA) was conducted under N$_2$ or air; both set of data were obtained at the scanning rate of 10° C./min. The results are summarized in Tables 2 and 3.

TABLE 2

Physical properties of homopolyimides derived from 2PE.ODA with various anhydrides: PMDA, sBPDA, OPDA, 6FDA, and BTDA,

| Sample ID | Dianhydride | $T_d^*$ (N$_2$; ° C.) | $T_d^*$ (Air ° C.) | $T_g$ (° C.) | $T_{onset}$ (° C.) | $T_{peak}$ (° C.) | ΔH (J/g) | Mn (kg/mol) | PDI |
|---|---|---|---|---|---|---|---|---|---|
| 05-89-1 | PMDA | 524.5 | 469.8 | N/A | 284.4 | 370.5 | 345.5 | 120.8 | 4.017 |
| 05-89-2 | s-BPDA | 545.1 | 479.3 | 251.1 | 296.0 | 357.3 | 339.3 | 80.3 | 2.555 |
| 05-90-1 | OPDA | 504.1 | 469.5 | 218.4 | 303.0 | 365.1 | 343.0 | 27.6 | 2.754 |
| 05-90-2 | 6FDA | 507.8 | 489.7 | 248.1 | 296.3 | 357.9 | 287.3 | 253.7 | 3.128 |
| 05-94-1 | BTDA | 540.7 | 522.5 | 240.0 | 294.2 | 352.7 | 301.2 | 84.4 | 3.056 |

TABLE 3

Properties of homopolyimides of various anhydrides with 2PE.MDA.

| Sample ID | Dianhydride | $T_d^*$ (N$_2$; ° C.) | $T_d^*$ (Air; ° C.) | $T_g$ (° C.) | $T_{onset}$ (° C.) | $T_{peak}$ (° C.) | ΔH (J/g) | $M_n$ (kg/mol) | PDI |
|---|---|---|---|---|---|---|---|---|---|
| 05-89-1 | PMDA | 509.5 | 492.6 | N/A | 303.6 | 387.9 | 364.5 | 83.1 | 3.934 |
| 05-89-2 | s-BPDA | 512.0 | 454.1 | 245.7 | 311.7 | 367.4 | 316.2 | 40.8 | 2.777 |
| 05-90-1 | OPDA | 507.2 | 474.7 | 215.9 | 304.3 | 368.4 | 336.7 | 27.9 | 2.445 |
| 05-90-2 | 6-FDA | 511.5 | 473.9 | 245.8 | 312.4 | 366.9 | 252.4 | 193.5 | 2.58 |
| 05-94-1 | BTDA | 518.6 | 517.7 | 240.5 | 301.6 | 361.6 | 319.4 | 68.9 | 3.334 |

Example 4-Synthesis of co-polyimides containing 20 mol % of 2PE.ODA, 2PE.MDA, 3PE.ODA or 4PE.ODA and 80 mol % of ODA. (a) Synthesis of ODA-80/2PE.ODA-20 copolymer In a 50 mL round-bottomed flask, 4,4'-oxydianiline (ODA, 0.3203 g; 1.6 mmol) and 0.1602 g (0.4 mmol) of 2PE-ODA (Example 1) were dissolved in 5 mL anhydrous N-Methyl-2-pyrrolidone (NMP), followed by the addition of 0.6204 g (2.0 mmol) of 4,4'-oxydi (phthalic anhydride), ODPA. The mixture was stirred at room temperature for 24 h, and 5 mL NMP was added. To the resulting poly(amic acid) mixture, 4.0 mL acetic anhydride and 3.2 mL pyridine were added. The polymerization mixture was stirred at room temperature under nitrogen for additional 24 hours. Finally, the polymerization mixture was poured into 300 mL of 2-propanol to precipitate the polyimide solids, which was collected on a filter funnel, and air dried. The crude polyimide product was then re-dissolved in 25 mL NMP and precipitated in 300 mL 2-propanol. The solids were collected on a filter funnel, air dried, and further dried in a vacuum oven at 0.5 torr, 130° C. for 24 hours.

(b) Synthesis of ODA-80/2PE.MDA-20 copolymer. Similar polymerization procedure and conditions were used with the following amounts for the monomers: (i) ODA, 0.3203 g (1.6 mmol); (ii) 2PE-MDA, 0.1594 g (0.4 mmol); ODPA, 0.6204 g (2.0 mmol).

(c) Synthesis of ODA-80/3PE.ODA-20 copolymer. Similar polymerization procedure and conditions were used with the following amounts for the monomers: (i) 0.3203 g (1.6 mmol) of ODA; (ii) 0.2002 g (0.4 mmol) 3PE-MDA; 0.6204 g (2.0 mmol) ODPA.

(d) Synthesis of ODA-80/4PE.ODA-20 copolymer. Similar polymerization procedure and conditions were used and conducted with the following amounts for the monomers: (i) ODA 0.3203 g (1.6 mmol); (ii) 4PE-MDA, 0.2403 g (0.4 mmol); ODPA, 0.6204 g (2.0 mmol).

TABLE 4

Physical/Thermal Properties of Homo- and Co-polyimides of ODPA, ODA, and 2PE.ODA.

| Sample ID | 2PE-ODA (mol %) | $T_d^*$ ($N_2$; ° C.) | $T_d^*$ (Air; ° C.) | $T_{g,int}$ (° C.) | $T_{onset}$ (° C.) | $T_{peak}$ (° C.) | ΔH (J/g) | $T_{g,cured}$ (° C.) | Mn (kg/mol) | PDI |
|---|---|---|---|---|---|---|---|---|---|---|
| 05-10-1 | 0 | 556.2 | 537.4 | 260.1 | N/A | N/A | N/A | 273.4 | 80.8 | 2.729 |
| 05-12-1 | 10 | 543.1 | 515.1 | 258.3 | 301.8 | 391.1 | 26.1 | 286.5 | 63.5 | 3.044 |
| 05-10-2 | 20 | 533.7 | 513.5 | 254.3 | 293.9 | 384.3 | 81.0 | 299.4 | 71.6 | 2.386 |
| 06-001-1 | 30 | 509.4 | 499.1 | 240.5 | 310.5 | 378.7 | 112.5 | 310.5 | 23.2 | 2.169 |
| 06-001-2 | 40 | 512.7 | 472.3 | 236.5 | 308.1 | 377.2 | 178.3 | 328.5 | 22.4 | 2.239 |
| 05-90-1 | 100 | 504.1 | 469.5 | 220.3 | 301.2 | 365.0 | 327.7 | N/A | 27.6 | 2.754 |

TABLE 5

Properties of Homo- and Copolyimides of ODPA, ODA and 2PE.MDA.

| Sample ID | 2PE-MDA (mol %) | $T_d^*$ ($N_2$; ° C.) | $T_d^*$ (Air; ° C.) | $T_{g,int}$ (° C.) | $T_{onset}$ (° C.) | $T_{peak}$ (° C.) | ΔH (J/g) | $T_{g,cured}$ (° C.) | Mn (kg/mol) | PDI |
|---|---|---|---|---|---|---|---|---|---|---|
| 05-10-1 | 0 | 556.2 | 537.4 | 260 | N/A | N/A | N/A | 273.4 | 80.8 | 2.729 |
| 05-13-2 | 10 | 542.3 | 547.4 | 258.8 | 335.0 | 405.1 | 44.4 | 289.1 | 53.1 | 2.493 |
| 05-13-1 | 20 | 524.5 | 493.3 | 256.9 | 328.5 | 401.2 | 90.1 | 308.6 | 133.5 | 2.128 |
| 06-002-1 | 30 | 519.3 | 517.8 | 238.5 | 333.3 | 399.8 | 128.0 | 334.6 | 20.1 | 2.186 |
| 06-002-2 | 40 | 515.6 | 501.4 | 235.0 | 313.8 | 384.6 | 160.2 | 350.0 | 20.3 | 2.233 |
| 05-13-2 | 100 | 507.2 | 474.7 | 330.5 | 330.5 | 330.5 | 330.5 | N/A | 27.9 | 2.445 |

Example 5-Synthesis of 6FDA-Based Homo- and Co-Polyimides Containing 2PE.ODA and APB (a) Synthesis of APB-6FDA (CP2) Homopolymer 1,3-Bis(3-aminophenoxy)benzene (APB, 1.169 g, 4.000 mmol) and DMAc (14.7 mL) were added to a 50 mL 3-necked flask equipped with a magnetic stirrer, nitrogen inlet and outlet, and stirred under dry nitrogen at room temperature for 30 min. 6FDA dianhydride (1.777 g, 4.000 mmol) was then charged. The light yellow solution was agitated at room temperature overnight to afford a viscous poly(amic acid) solution. This solution was diluted with DMAc (4-6 mL), poured into a glass dish, followed by vacuum evaporation of DMAc at 50° C., and heat-treated at: 100° C./1 hr, 150° C./1 hr, 175° C./1 hr, 200° C./1 hr, 250° C./1 hr and 300° C./1 hr to form imidized CP2 films. The film thickness was approximately 50-150 μm. ATR-IR (cm$^{-1}$): 3077, 1785, 1719, 1585, 1478, 1452, 1474, 1236, 1188, 1140, 1092, 962, 845, 780, 719, 627, 591, 568, 544, 527.

(b) Synthesis of APB-6FDA-2PE.ODA-25 copolymer. APB (0.8768 g, 3.000 mmol), 2PE.ODA (0.4004 g, 1.000 mmol) and DMAc (15 mL) were added to a 50 mL 3-necked flask equipped with a magnetic stirrer, nitrogen inlet and outlet, and stirred under dry nitrogen at room temperature for 30 min. 6FDA (1.777 g, 4.000 mmol) was then charged. The light yellow solution was agitated at room temperature for 24 hr to afford a poly(amic acid) solution. The mixture poured into a glass dish, followed by vacuum evaporation of DMAc at 50° C., and heat-treated at: 100° C./1 h, 150° C./1 h, 175° C./1 h, 200° C./1 h, and 250° C./1 h to form polyimide films. The film thickness was approximately 20-100 μm. ATR-IR (cm$^{-1}$): 3078, 2212 (C≡C), 1784, 1720 (C=O), 1586, 1478, 1369, 1238, 1189, 1097, 964, 845, 780, 718, 683, 626. This procedure was followed to prepare other 2PE-BPE-x copolymer (x stands for percentage of 2PE.ODA diamine).

(c) Synthesis of APB-6FDA-2PE.ODA-50 copolymer. Similar polymerization procedure and conditions to prepare APB-6FDA-2PE.ODA-25 copolymer were used and conducted with the following amounts for the monomers: APB (0.5846 g, 2.000 mmol), 2PE.ODA (0.8009 g, 2.000 mmol) and 6FDA (1.777 g, 4.000 mmol). ATR-IR (cm$^{-1}$): 3071, 2213 (C≡C), 1784, 1724 (C=O), 1587, 1478, 1370, 1298, 1238, 1190, 1157, 1141, 1125, 1095, 1002, 844, 755, 718, 687, 626, 593, 567.

(d) Synthesis of APB-6FDA-2PE.ODA-75 copolymer. Similar polymerization procedure and conditions to prepare APB-6FDA-2PE.ODA-25 copolymer were used and conducted with the following amounts for the monomers: APB (0.2923 g, 1.000 mmol), 2PE.ODA (1.2013 g, 3.000 mmol) and 6FDA (1.777 g, 4.000 mmol). ATR-IR (cm$^{-1}$): 3072, 2211 (C≡C), 1783, 1722 (C=O), 1586, 1478, 1370, 1298, 1238, 1190, 1157, 1141, 1125, 1095, 1002, 844, 755, 718, 687, 626.

(e) Synthesis of 6FDA-2PE.ODA-100 homopolymer. 2PE.ODA (1.6017 g, 4.000 mmol) and DMAc (15 mL) were added to a 50 mL 3-necked flask equipped with a magnetic stirrer, nitrogen inlet and outlet, and stirred under dry nitrogen at room temperature for 30 min. 6FDA (1.777 g, 4.000 mmol) was then charged. The light yellow solution was agitated at room temperature for 24 hr to afford a poly(amic acid) solution. The mixture poured into a glass dish, followed by vacuum evaporation of DMAc at 50° C., and heat-treated at: 100° C./1 h, 150° C./1 h, 175° C./1 h, 200° C./1 h, and 250° C./1 h to form polyimide films. The film thickness was approximately 20-100 μm. ATR-IR (cm$^{-1}$): 3063, 2213 (C≡C), 1778, 1722 (C=O), 1605, 1495, 1477, 1417, 1373, 1337, 1297, 1236, 1207, 1094, 963, 842, 814, 754, 717, 687, 637, 596, 566.

TABLE 6

Properties of Homo- and Copolyimides of 6FDA, ODA and 2PE.ODA.

| Sample Name | 6FDA | 2PE.ODA (x) | APB (100-x) | $T_{g,int}$ $^a$ (° C.) | $T_{g,cured}$ $^b$ (° C.) | $T_{d5\%}$ $^c$ (° C.) in air | $T_{d5\%}$ $^c$ (° C.) in N$_2$ |
|---|---|---|---|---|---|---|---|
| APB-6FDA (CP2) | 100 | 0 | 100 | 205 | NA$^c$ | 526 | 530 |
| APB-6FDA-2PE.ODA-25 | 100 | 25 | 75 | 210 | 238 | 504 | 515 |
| APB-6FDA-2PE.ODA-50 | 100 | 50 | 50 | 220 | 286 | 484 | 512 |
| 6FDA-2PE.ODA | 100 | 100 | 0 | 248 | >400 | 396 | 496 |

Example 6. 3D Article fabricated by Scanning Laser Sintering (SLS). The resin powder may be fused in the sintering/melting step by various heat sources and processes, including SLS using a laser as an energy source to melt/sinter the resin. SLS is done using a SLS machine, which can include a laser for emitting laser radiation and a scanner system for directing the laser radiation. The machine may include a powder delivery platform and a build platform. The powder resin may be arranged on the powder delivery platform, which may move up to present some of the powder to a roller or arm, which may move a portion of the powder onto the build platform to form a layer of the powder (powder layer) on the build platform. The laser and scanner system is then operated to direct the laser radiation onto the layer of the powder to selectively melt/sinter a portion of the layer of the mixture to form a fused layer of the powder on the build platform. The powder delivery platform may then move up to present additional powder to the roller or arm. These steps may be repeated to successively build a plurality of fused layers, each of which fuse by laser energy to the previously formed fused layer, in order to form a 3D component. The 3D component, formed by the layer-by-layer buildup of the plurality of fused layers in this additive manufacturing process, may be surrounded by a powder bed of the powder, which has not been sintered/melted by the laser radiation. Thereafter, the 3D component may be removed from the powder bed and subjected to a further heating process in order to fully cure the resin in the 3D component to form a 3D final component. The 3D component may be formed following a predetermined model of the 3D component as present in a computer aided design (CAD) file, which model may be used to control the scanner system for directing the laser radiation upon each layer of the mixture. The resin powder may have a particle size distribution where 80-90% of the particles have a size of 25-120 µm, or 40-100 µm; with a single particle size distribution peak or mean at 50-100 microns as measured by a laser particle size analyzer.

(a) Sintering/Melting. The mixture may be sintered/melted to form the 3D component. Such sintering/melting may be accomplished by exposing the powder to a heat source including for example, laser radiation. Exposure to such heat source causes the resin in the mixture to sinter/melt, and then fused upon cooling to form the matrix that is a solid or porous mass. The sintering/melting step may be performed using an SLS machine. As part of the SLS process, the resin powder may be taken from the powder delivery platform, and then spread onto the build platform using the roller or arm, so as to form a powder layer having a thickness of 100-150 µm. The laser beam from the laser is selectively irradiated on a predetermined area of the powder layer by the scanner system, in order to melt/sinter the resin in the predetermined area of the powder layer, thus forming a fused layer of the mixture in the powder layer. The laser in the SLS system may be $CO_2$ laser, which may be operated at a power of 25-38 watts. The build platform then moves down by one layer thickness (i.e. 100-150 µm) and the powder delivery platform moves up to expose more of the mixture on the powder delivery platform to the roller or arm. This process of spreading the resin powder, selectively irradiating the mixture, moving the build platform down, and moving the powder delivery platform up is successively repeated to build up additional fused layers on top of the prior fused layers, where each successive fused layer fuses with the previously-formed fused layer to form a 3D green component in the powder bed. In this process, the presently-formed fused layer may fuse with the previously-formed fused layer, and so on, during the laser sintering of the presently-formed fused layer. This may result in the layer-by-layer buildup of the 3D component. Such layer-by-layer process of building the 3D component may operate automatically by computer control of the scanner system of the SLS machine, where the area of the powder layer to be irradiated may be determined according to cross-sectional data of a model of the 3D green component from a CAD file. Upon completion of this process, the un-sintered powder on the build platform forms the powder bed that surrounds the 3D component contained within it, and both may be allowed to cool before being removed from the build platform.

In the SLS process of printing the 3D component, a powder bed temperature on the build platform may be in the range of 150-250° C. A feed temperature of the mixture on the delivery platform may be in the range of 80-120° C. These temperature ranges may be based on a total melting behavior displayed by the imide resin being between 150-260° C., which melting temperature thus enables the powder bed temperature to be 150-240° C. These temperatures may vary depending on the type of resin used and may be based on a DSC thermogram for the type of resin powder being used.

Curing. The 3D component is then heated to completely cure the resin including the reactive PEPA endcaps. Such curing fully crosslinks the reactive PEPA-terminal groups to form a consolidated network as the 3D final component. The 3D final component is a polyimide thermoset. The 3D final component may be suitable for use in high-temperature environments, and may have a service temperature of greater than 300° C. As such, the 3D final component may be used without thermal degradation in applications reaching temperatures from 250-300° C.

The cure cycle or heating schedule and heating apparatus used to heat the 3D component and completely cure the resin are not particularly limited. The heating schedule, including the temperature(s) to which the 3D component is heated, may depend on the type of resin used. The heating schedule may include exposure to an elevated temperature, a single gradual increase in temperature, more than one increases in temperature, two increases in temperature separated by a decrease in temperature, or other variations of heating, cooling, and soaking. The 3D component may be held ("soaked") at a certain temperature for a predetermined amount of time so that an entirety of mass of the 3D component reaches a temperature that is at equilibrium with the surrounding environment. Heating of the 3D component in the curing step may be accomplished using any suitable heating apparatus including for example, an oven (e.g. air-circulation oven), furnace, infrared heat source, a flame, plasma, laser, other heat source, or combinations thereof.

In an exemplary embodiment, the 3D component is heated at a rate of 1-5° C./minute from an initial ambient temperature to slightly below the softening temperature ($T_g$) of the resin. The heating schedule includes multiple holds at various predetermined temperatures (predetermined soak temperatures) for a predetermined amount of time. The 3D component is then heated to a final temperature of 370° C. for 1-2 hours to form a crosslinked network of polymer the 3D final component. Such heating schedule may inhibit a dimensional change occurring by heating the 3D component to form the 3D final component, which may otherwise occur due to softening of the resin in the 3D component at elevated temperatures during the curing step.

Post Processing

The mixture, the 3D green component, and/or the 3D final component may be subject to additional processing steps, including but not limited to pressing, stamping, cooling, coating, or subtractive machining processes such as milling, grinding, cutting, etc.

Example 7. 3D Article fabricated by Fused Deposition Modeling technique (FDM). The two most common techniques used for AM are fused filament fabrication (FFF), which is also known as fused deposition modeling (FDM), and selective laser sintering (SLS). FFF generally requires the polymer to be in the form of a tightly controlled filament with a typical diameter of 1.75 mm (+0.25 mm), while SLS generally requires the polymer to be in the form of a uniform size distribution fine powder. While the focus of embodiments of the present invention described herein is on FFF and SLS, e.g., making a filament of previously un-extrudable high crosslink density thermosetting polyimides and allowing SLS on powders that behave similar to conventional thermoplastic materials such as Ultem® or polyetherether ketone (PEEK) when melt-processed with a laser, the application of the composition and materials is not limited thereto.

Thus, in accordance with an embodiment of the present invention an additive manufacturing process for preparing a three dimensional article is provided. The method may include one or more of the following steps: forming a phenylethynyl-functionalized polyimide material; partially curing the phenylethynyl-functionalized polyimide material to a degree of curing that is in a range from about 5 percent to about 30 percent; depositing a plurality of layers comprising the partially-cured phenylethynyl-functionalized polyimide material to form a 3D article; and heating the 3D article to a temperature up to, but not exceeding, a first glass transition temperature and maintaining the temperature for a sufficient time to advance the degree of curing.

Filament feedstock. In the case of the phenylethynyl-functionalized polyimide material disclosed in this invention, a DACA twin screw extruder may be used for smaller amounts of materials (5-10 g). According to an embodiment, filaments comprising partially-cured phenylethynyl-functionalized polyimides having a degree of cross-linking. Once a flexible filament of high phenylethynyl content polyimide is made, it can be fed into a fused deposition modeling head of an FFF or FDM machine. The requisite high temperature (e.g., >300° C.) PE crosslink chemistry in this invention prevents the material to completely crosslink during the printing process, but allows the operator to tune in a critical amount of crosslink density (FDM at temperatures >260° C.) that enables the material to be self-supporting upon further post processing into a fully cross-linked part.

An FDM machine used in this invention is a 3Dn 500 Quad Head from n-Scrypt with a fused filament head (n-FD pump) that can operate up to 425° C.

Samples were initially tested for rheology and viscosity to pull fibers via simple melting and pulling fibers/filaments from the melt. The sample with high crosslink density and with an inherent lower molecular weight cannot be pulled into a fiber. However, the phenylethynyl-functionalized polyimides of the present invention with high crosslink density and tunable molecular weight can be pulled into a fiber. Materials that matched this requirement were tested in the extruder. A DACA Instruments benchtop twin-screw extruder was used to make filaments with approximately 1.75 mm diameter for test runs. Polyimide thermosetting polymer was ground into a powder for feeding into the hopper of the extruder. A 1.75 mm diameter die was attached to the extruder opening in closed position. The extruder was pre-heated to 220° C. (controlled via N2 gas flow at 10 psi) and material was added and pushed into the hopper. At the same time, the twin-screws were ramped to 100 RPM over a period of 30 seconds and material fed and pushed into the moving screw assembly. The residence time of the material in the twin-screw assembly at 220° C. was approximately 1 min. The die port was opened to release a filamentary material into a container. The diameter of the filament was approximately 1.5 mm to 1.75 mm. Filaments long enough for feeding into an n-Scrypt fused filament fabrication system were obtained.

Post cure example to reach 100% degree of cure (fully crosslinked). Printed coupons were exposed at 220° C. to 300° C. with 10° C. increments up to 325° C. The samples were cured for one hour at each temperature. Samples were then heated from 325° C. to 370° C. at a rate of 1° C./min. At each temperature coupons were pulled out for DSC to measure degree of cure. DSC was performed at 10° C./min from 40° C. to 550° C. using ~15 mg sample size. Fused deposition modeled articles retained their shape after conducting this cure cycle.

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

What is claimed is:

1. A process of making a cross-linkable thermoplastic polymer comprising:
   a) thermally imidizing and/or chemically imidizing a solution of polyamic acid formed from a solution of monomers comprising:
      i) a first monomer having the following structure:

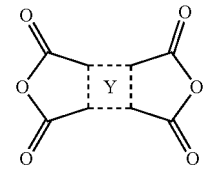

Y is selected from one of the following moieties:

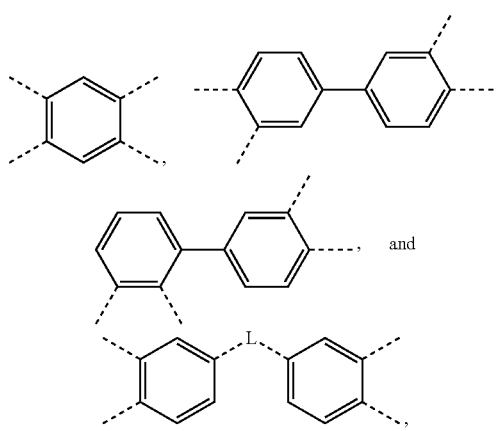

where L is a bivalent linker selected from the one of following moieties: O, C=O, $SO_2$, $C(CF_3)_2$, $C(CF_3)$ Ph, and —O-($pC_6H_3$)—$C(CF_3)_2$-($pC_6H_4$)—O—;

ii) a second monomer having the following structure:

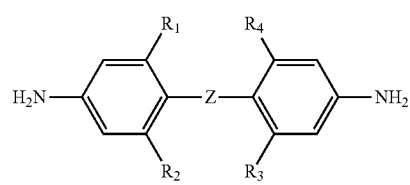

each Z is independently O, $CH_2$, or C=O;

at least one of $R_1$, $R_2$, $R_3$ and $R_4$ is phenylethynyl, with the remainder of $R_1$, $R_2$, $R_3$ and $R_4$ each independently being H or phenylethynyl:

iii) optionally a third monomer having the following structure:

H₂N—Ar—NH₂ wherein Ar is:

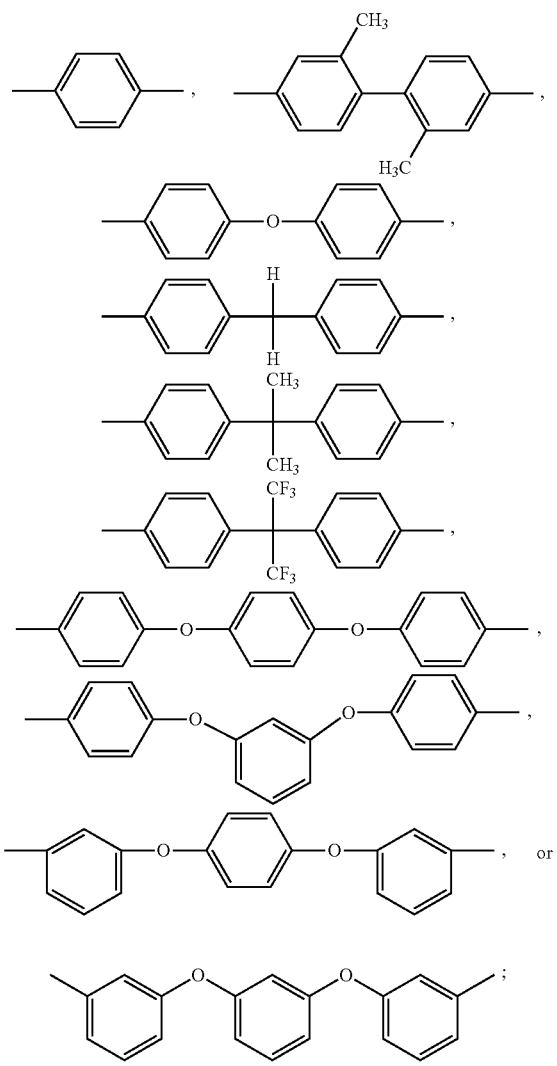

and
iv) an aprotic polar solvent;
wherein said monomer solution comprises a molar ratio of said first monomer to combination of said second and third monomer of from about 0.8:1 to about 1.2:1, and the total weight percent, based on total monomer solution weight, of said first, second and third monomers is from about 2% to about 40%,
thereby forming a solution of polymer in the aprotic polar solvent, said polymer having the following structure:

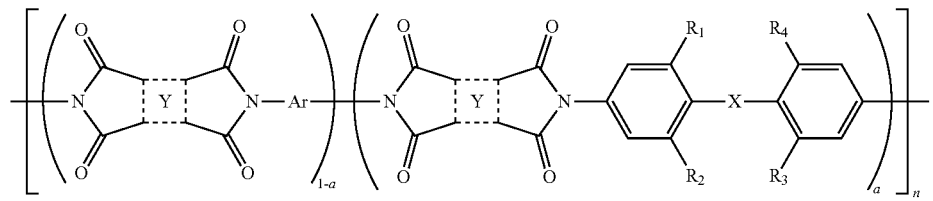

wherein
each X is independently $O_2$, $CH_2$, or C=O;
at least one of $R_1$, $R_2$, $R_3$ and $R_4$ is phenylethynyl, with the remainder of $R_1$, $R_2$, $R_3$ and $R_4$ each independently being H or phenylethynyl;
each Y is independently selected from one of the following moieties:

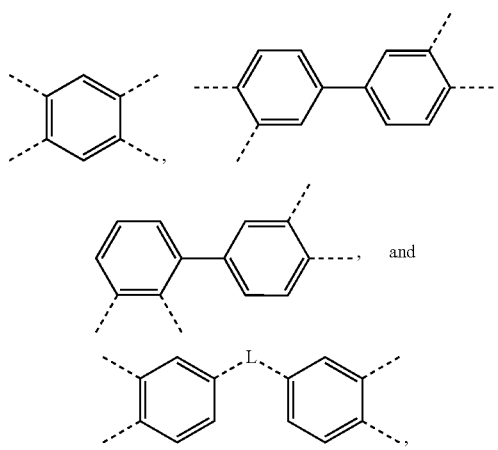

where each L is independently a bivalent linker selected from the one of following moieties: O, C=O, $SO_2$, $C(CF_3)_2$, $C(CF_3)Ph$, and —O-($pC_6H_4$)-$C(CF_3)_2$-($pC_6H_4$)-O-;
each Ar is independently:

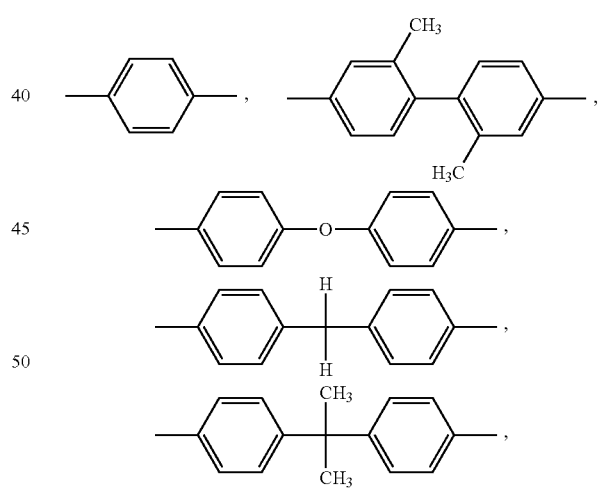

-continued

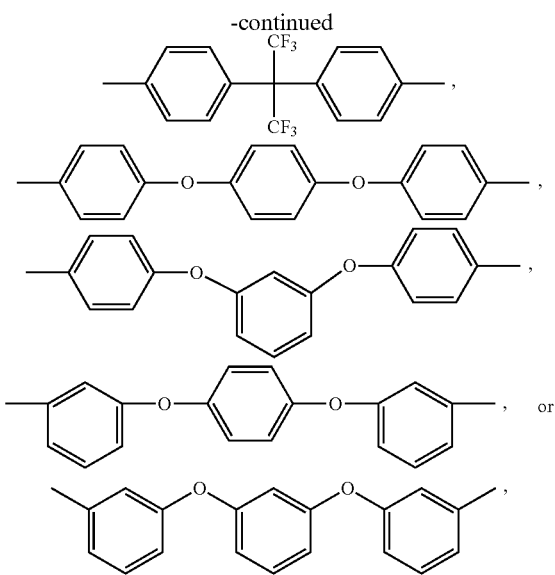

each a is from 0.01 to 1; and n is an integer from about 3 to about 200;
b) precipitating said polymer out of said polymer solution; and
c) removing the precipitated polymer from solvent.

2. The process of claim 1, wherein:
a) said aprotic polar solvent is selected from the group consisting of dimethylacetamide, 1-methyl-2-pyrrolidinone and mixtures thereof;
b) said first monomer and combination of said second and third monomer are present in said momomer solution in a molar ratio of from about 0.95:1 to about 1.05:1;
c) the total weight percent, based on total momomer solution weight, of said first, second and third monomers is from about 10% to about 25%; and
d) precipitating said polymer out of said solution, comprises combining said solution with a nonsolvent.

3. The process of claim 1, wherein:
a) said aprotic polar solvent is selected from the group consisting of dimethylformamide, dimethylacetamide, 1-methyl-2-pyrrolidinone and mixtures thereof;
b) said first monomer and combination of said second and third monomer are present in said momomer solution in a molar ratio of from about 0.9:1 to about 1.1:1;
c) the total weight percent, based on total momomer solution weight, of said first, second and third monomers is from about 5% to about 35%; and
d) precipitating said polymer out of said polymer solution, comprises adding said solution to said nonsolvent.

4. The process of claim 2, wherein said nonsolvent is selected from the group consisting of water, methanol, ethanol, 2-propanol and mixtures thereof.

5. The process of claim 1 wherein said third monomer is present in said momomer solution in a molar ratio of said second monomer to third monomer of from about 0.001:0.999 to about 0.999:0.001.

6. The process of claim 1 wherein said third monomer is present in said momomer solution in a molar ratio of said second monomer to third monomer of from about 0.01:0.99 to about 0.99:0.01.

7. The process of claim 1 wherein said third monomer is present in said momomer solution in a molar ratio of said second monomer to third monomer of from about 0.1:0.9 to about 1:1.

8. The process of claim 1 wherein:
a) said thermally imidizing comprises heating said polyamic acid solution to within a temperature that is from 50° C. below said solution's boiling point to said solution's boiling point; and
b) said chemical imidizing comprises adding a dehydrating agent and a base to said polyamic acid solution; and holding said solution at a temperature of from about 0° C. to about 120° C. for at said temperature for about three hours to about 48 hours.

9. The process of claim 8 wherein:
a) said thermally imidizing comprises heating said solution to within a temperature that is from 20° C. below said solution's boiling point to said solution's boiling point and holding said solution at said temperature for about three hours to about 24 hours and adding an azeotropic agent to said solution before or during heating said solution; and
b) said dehydrating agent is selected from the group consisting of acetic anhydride, trifluoroacetic anhydride and mixtures thereof, and said base is selected from the group consisting of pyridine, trimethylamine, 2-picoline and mixtures thereof; and said solution is held at said temperature for about 12 hours to about 24 hours.

10. The process of claim 9 wherein:
a) said solution is held at said temperature for about 8 hours to about 24 hours, and said azeotropic agent is added to said solution before heating; and
b) said solution is held at said temperature for about 18 hours to about 24 hours.

11. The process of claim 10 wherein said azeotropic agent is selected from the group consisting of toluene, xylene and mixtures thereof.

* * * * *